United States Patent
Barzilay et al.

(10) Patent No.: US 11,229,600 B2
(45) Date of Patent: Jan. 25, 2022

(54) COMPOSITIONS AND METHODS FOR SELECTIVE GI TRACT DELIVERY

(71) Applicant: VITAL BEVERAGES GLOBAL INC., Tortola (VG)

(72) Inventors: Amir Barzilay, Kokhav Yair (IL); Dorit Rozner, Gedera (IL)

(73) Assignee: VITAL BEVERAGES GLOBAL INC., Tortola (VG)

( * ) Notice: Subject to any disclaimer, the term of this patent is extended or adjusted under 35 U.S.C. 154(b) by 0 days.

(21) Appl. No.: 15/513,672

(22) PCT Filed: Sep. 20, 2015

(86) PCT No.: PCT/IL2015/050951
§ 371 (c)(1),
(2) Date: Mar. 23, 2017

(87) PCT Pub. No.: WO2016/046817
PCT Pub. Date: Mar. 31, 2016

(65) Prior Publication Data
US 2017/0290768 A1    Oct. 12, 2017

Related U.S. Application Data

(60) Provisional application No. 62/054,456, filed on Sep. 24, 2014.

(51) Int. Cl.
*A61K 9/00* (2006.01)
*A61K 9/50* (2006.01)
(Continued)

(52) U.S. Cl.
CPC .............. *A61K 9/0095* (2013.01); *A23L 2/52* (2013.01); *A23L 33/40* (2016.08); *A61K 9/0053* (2013.01);
(Continued)

(58) Field of Classification Search
None
See application file for complete search history.

(56) References Cited

U.S. PATENT DOCUMENTS 5,160,742 A * 11/1992 Mazer .................. A61K 9/5052
424/469
6,022,562 A    2/2000 Autant et al.
(Continued)

FOREIGN PATENT DOCUMENTS

EP         1172100 A1     1/2002
WO      2006039022 A2     4/2006
(Continued)

OTHER PUBLICATIONS

TA van Beek, P Montoro. "Chemical analysis and quality control of Ginkgo biloba leaves, extracts, and phytopharmaceuticals." Journal of Chromatography A, vol. 1216, 2009, pp. 2002-2032. (Year: 2009).*

(Continued)

*Primary Examiner* — Isaac Shomer
(74) *Attorney, Agent, or Firm* — The Roy Gross Law Firm, LLC; Roy Gross

(57) ABSTRACT

A composition-of-matter is provided. The present composition includes dietary supplements capable of reducing or reversing the negative effects of alcohol on motor and cognition, dietary supplements having anti-gastroparesis, antiemetic, analgesic and anti-inflammatory activities and/or dietary supplements capable of increasing alcohol catabolism and decreasing the level of toxic products of alcohol catabolism.

16 Claims, 8 Drawing Sheets

(51) Int. Cl.

| | |
|---|---|
| *A23L 33/00* | (2016.01) |
| *A23L 2/52* | (2006.01) |
| *A61K 9/10* | (2006.01) |
| *A61K 36/9068* | (2006.01) |
| *A61K 36/76* | (2006.01) |
| *A61K 31/12* | (2006.01) |
| *A61K 31/4748* | (2006.01) |
| *A61K 31/198* | (2006.01) |
| *A61K 31/05* | (2006.01) |
| *A61K 31/355* | (2006.01) |
| *A61K 31/352* | (2006.01) |
| *A61K 31/365* | (2006.01) |
| *A61K 31/525* | (2006.01) |
| *A61K 31/7004* | (2006.01) |
| *B65D 81/32* | (2006.01) |

(52) U.S. Cl.
   CPC ............... *A61K 9/10* (2013.01); *A61K 9/501* (2013.01); *A61K 9/5015* (2013.01); *A61K 9/5047* (2013.01); *A61K 9/5052* (2013.01); *A61K 9/5063* (2013.01); *A61K 9/5084* (2013.01); *A61K 31/05* (2013.01); *A61K 31/12* (2013.01); *A61K 31/198* (2013.01); *A61K 31/352* (2013.01); *A61K 31/355* (2013.01); *A61K 31/365* (2013.01); *A61K 31/4748* (2013.01); *A61K 31/525* (2013.01); *A61K 31/7004* (2013.01); *A61K 36/76* (2013.01); *A61K 36/9068* (2013.01); *B65D 81/32* (2013.01); *A23V 2002/00* (2013.01)

(56) References Cited

U.S. PATENT DOCUMENTS

| | | | | |
|---|---|---|---|---|
| 6,261,279 | B1* | 7/2001 | Demopulos | A61K 31/00 604/500 |
| 6,340,478 | B1* | 1/2002 | Blatt | A61K 9/5047 424/451 |
| 6,365,148 | B1* | 4/2002 | Kim | A61K 9/5073 424/93.1 |
| 6,672,755 | B1* | 1/2004 | Potter | B01F 5/248 366/174.1 |
| 8,163,307 | B2 | 4/2012 | Bechet et al. | |
| 2002/0106408 | A1* | 8/2002 | Bacon | A61K 9/286 424/471 |
| 2003/0096791 | A1* | 5/2003 | Gupte | A61K 9/5078 514/57 |
| 2005/0090557 | A1* | 4/2005 | Muhammad | A61K 9/0014 514/627 |
| 2006/0045865 | A1* | 3/2006 | Jacob | A61K 9/204 424/78.27 |
| 2006/0204576 | A1* | 9/2006 | Petereit | A61P 29/00 424/472 |
| 2007/0202215 | A1 | 8/2007 | Lak | |
| 2008/0020018 | A1* | 1/2008 | Moodley | A61K 9/5073 424/433 |
| 2009/0048345 | A1* | 2/2009 | Lee | A61K 9/2873 514/570 |
| 2009/0274754 | A1* | 11/2009 | Cipolla | A61K 47/22 424/450 |
| 2010/0104675 | A1* | 4/2010 | Kizelsztein | A61P 25/00 424/773 |
| 2010/0189767 | A1* | 7/2010 | Shimoni | C12N 1/04 424/439 |
| 2010/0196554 | A1 | 8/2010 | Rivera et al. | |
| 2010/0247639 | A1* | 9/2010 | Ravishankar | A23L 27/72 424/456 |
| 2010/0273773 | A1* | 10/2010 | Gijsen | C07D 223/20 514/211.11 |
| 2011/0229562 | A1* | 9/2011 | Bar | A61P 9/06 424/452 |
| 2011/0229590 | A1* | 9/2011 | Kim | A61P 9/10 424/756 |
| 2012/0263828 | A1* | 10/2012 | Ackley | A23L 2/52 426/73 |
| 2012/0315334 | A1* | 12/2012 | Lizio | A61K 9/1676 424/490 |
| 2013/0034632 | A1* | 2/2013 | Cuomo | A23P 10/28 426/96 |
| 2015/0190348 | A1* | 7/2015 | Haksar | A61K 9/1623 424/463 |
| 2015/0209298 | A1* | 7/2015 | Haksar | A61K 9/5073 424/463 |

FOREIGN PATENT DOCUMENTS

| | | | | |
|---|---|---|---|---|
| WO | 2009079537 A1 | | 6/2009 | |
| WO | WO-2010034342 A1 | * | 4/2010 | ............. A61P 25/32 |
| WO | 2012013994 A2 | | 2/2012 | |
| WO | WO-2012082631 A | * | 6/2012 | ............. A23P 10/30 |
| WO | WO-2012116445 A1 | * | 9/2012 | ........... A61K 9/0056 |
| WO | WO-2015054302 A1 | * | 4/2015 | ............. A61P 25/16 |

OTHER PUBLICATIONS

J-M Lu, Q Yao, C Chen. "Ginseng Compounds: An Update on Their Molecular Mechanisms and Medical Applications." Current Vascular Pharmacology, vol. 7(3), Jul. 2009, original pp. 293-302. NIH Public Access Author Manuscript, pp. 1-18, available in Pubmed Central Aug. 25, 2010. (Year: 2010).*

SK Jain, A Jain. "Target-specific drug release to the colon." Expert Opinion in Drug Delivery, vol. 5(5), 2008, pp. 483-498. (Year: 2008).*

AG Gaonkar, N Vasisht, AR Khare, R Sobel. "Microencapsulation in the Food Industry A Practical Implementation Guide." Book published by Elsevier, Available Jul. 4, 2014. Front matter and p. 527 provided. (3 printed pages). (Year: 2014).*

NS Dey, S Majumdar and MEB Rao. "Multiparticulate Drug Delivery Systems for Controlled Release." Tropical Journal of Pharmaceutical Research, Sep. 2008; 7(3), pp. 1067-1075. (Year: 2008).*

Peter R. Shewry and Arthur S. Tatham. "The prolamin storage proteins of cereal seeds: structure and evolution." Biochemical Journal, vol. 267, 1990, pp. 1-12. (Year: 1990).*

Jacob Bouman, Peter Belton, Paul Venema, Erik van der Linden, Renko de Vries, Sheng Qi. "Controlled Release from Zein Matrices: Interplay of Drug Hydrophobicity and pH." Pharmaceutical Research, vol. 33, 2016, pp. 673-685. (Year: 2016).*

International Search Report of PCT/IL2015/050951 Completed Dec. 27, 2015; dated Dec. 28, 2015; 8 Pages.

Written Opinion of PCT/IL2015/050951 Completed Dec. 27, 2015; dated Dec. 28, 2015; 6 Pages.

* cited by examiner

COMPOSITIONS AND METHODS FOR SELECTIVE GI TRACT DELIVERY

CROSS-REFERENCE TO RELATED APPLICATIONS

This application is a national phase of PCT Patent Application No. PCT/IL2015/050951, filed Sep. 20, 2015, which claims the benefit of priority of U.S. Provisional Patent Application No. 62/054,456, filed Sep. 24, 2014 entitled COMPOSITIONS AND METHODS FOR SELECTIVE GI TRACT DELIVERY. The contents of the above applications are all incorporated by reference as if fully set forth herein in their entirety.

FIELD AND BACKGROUND OF THE INVENTION

The present invention relates to compositions and methods of using same for selective delivery of active ingredients in the GI tract. Embodiments of the present invention relate to a liquid (aqueous) preparation incorporating soluble and/or suspended bioactive ingredients for remedying the effects of excessive alcohol consumption.

Alcohol is the most popular legal intoxicant around the globe. The current global market for alcoholic beverages is in excess of $900B a year. In Europe, for example, the average daily consumption of alcohol per person is in excess of 40 grams of pure alcohol. This average daily alcohol consumption quantity is comparable to the consumption of 3 beers.

Alcohol consumption intoxicates the human body and results in a wide variety of short term and not infrequently long term negative side effects and outcomes. The first metabolic intermediate generated through alcohol metabolism in the human body is acetaldehyde, a toxic compound even at very low concentrations. Therefore, in order to avoid irreversible short term health damages and optionally death, the rate of alcohol metabolism by the human body is limited by its ability to metabolize and remove blood and/or cell-attached and/or tissue-attached acetaldehyde. As a result, the rate of blood alcohol metabolism is quite slow, typically ranging between 0.03-0.15 gram percent per hour by occasional alcohol consumers, and up to 0.15-0.25 gram percent per hour by binge and alcoholic drinkers.

Alcohol significantly impairs both motor and cognitive performance. The most critical activity impaired by blood alcohol and blood acetaldehyde is driving, which is materially negatively affected by the effect of alcohol and acetaldehyde on the brain, resulting in reduced cognitive and motor performance, and further accompanied by the impairment of judgment and sliding into reckless behavior and undesired risk taking. Yet, only lately, a series of clinical research studies found out, that while motor function following alcohol consumption is more quickly restored when BAC level is on the decreasing slope, cognitive performance and maintenance of reckless behavior/risk taking significantly lags behind it. This means, that the alcohol intoxicated individual subjectively feels recovered from the intoxicating effects of excess alcohol consumption, where in reality, the impaired cognitive judgment and response functions are still far from normal. This phenomena is true in many cases where the blood alcohol levels are already within legal limits in many countries around the globe. This gap between motor performance recovery and cognitive (and judgment) performance recovery is a major reason why cognitive function' impaired drinkers make a decision to enter their car and drive, leading—in an ineligible number of events—to severe and not infrequently—lethal accidents.

Several products in the market attempt to resolve some of the negative outcomes of excess alcohol consumption. These products are frequently powder-based products, which need to be reconstituted into liquid (typically water) prior to its consumption. Examples of such products are Sobrietol™, Party Smart™, Drinkin' Mate™, NOHO™, RU-21™, Hangover Hater™, AL-neutralizer™, Hangover Joe's, etc. The target of most products on the market is to alleviate the morning-after hangover symptoms. With very similar compositions—mainly B+C vitamins, minerals and amino acids, these products target the replenishment of the body of the depletion of these important compounds during excess blood alcohol metabolism. Sobrietol™ takes a different approach, by incorporating alcohol metabolizing enzymes, which target the decomposition of the consumed alcohol in the stomach and intestines, and thus reduce the absorption of alcohol into systemic circulation. Naturally, a person needs to consume Sobrietol prior to alcohol consumption, in order for the Sobrietol™ product to demonstrate some level of efficacy. A third approach is taken by Party Smart™. This product incorporates a number of plant extracts, which claim targeting the protection of liver damage through anti-oxidant activities and through affecting increased alcohol metabolizing enzymes' activity. Similar to the other above-mentioned products, Party Smart™ needs to be consumed prior to alcohol consumption. Human data demonstrating the impact of these products on hangover and blood alcohol is very limited, or demonstrate very limited efficacy.

Therefore, there remains a need for a composition-of-matter that can be used to remedy the negative effects of excess alcohol consumption.

SUMMARY OF THE INVENTION

According to one aspect of the present invention there is provided a composition-of-matter comprising at least two types of microparticles each formed from an active ingredient core encapsulated by at least one coating material, the at least two types of said microparticles being differentiated by the active ingredient or the at least one coating material.

According to further features in preferred embodiments of the invention described below each of the at least two types of said microparticles is capable of releasing the active ingredient at a different region of a GI tract.

According to still further features in the described preferred embodiments the microparticles have a diameter of 25-100 microns.

According to still further features in the described preferred embodiments the active ingredient core of the composition-of-matter comprises at least one of: (a) dietary supplements having cognitive and motor function; (b) dietary supplements having anti-gastroparesis, antiemetic, analgesic and anti-inflammatory activities; and/or (c) dietary supplements being capable of increasing alcohol catabolism.

According to still further features in the described preferred embodiments the composition-of-matter comprises (a) and (b), (b) and (c) or (a) and (c).

According to still further features in the described preferred embodiments at least some of the dietary supplements of (a)-(c) are encapsulated within microparticles.

According to still further features in the described preferred embodiments the composition-of-matter is formulated as a beverage.

According to still further features in the described preferred embodiments the composition-of-matter is formulated as a gel.

According to still further features in the described preferred embodiments a pH of the beverage or the gel is 2.4-3.5.

According to still further features in the described preferred embodiments, the beverage or gel do not contain enzymes.

According to further features in the described embodiments, the dietary supplements having cognitive and motor function are selected from the group having antagonistic activity against GABA, Adenosine A1, AchE, Dopamine D1, Dopamine D2, Dopamine D3, 5-HT1A, 5-HT2 and 5HT3; and; agonistic activity against Glutamate, Adenosine A2A, 5-HT1B and 5-HT4

According to still further features in the described preferred embodiments the dietary supplement having antagonistic activity against GABA is selected from the group consisting of Bilobalide, Ginkgolides (A, B & C), Puerarin, Resveratrol, Quercetin, Curcumin, Caffeine, Theophylline, Amentoflavone, Dihydromyricetin and Copper Glycinate Chelate.

According to still further features in the described preferred embodiments the dietary supplement having antagonistic activity against Adenosine A1 is selected from the group consisting of Caffeine and Theophylline.

According to still further features in the described preferred embodiments the dietary supplement having antagonistic activity against AchE is selected from the group consisting of Huperzine A and Rosmarinic acid.

According to still further features in the described preferred embodiments the dietary supplement having antagonistic activity against Dopamine D1 is selected from the group consisting of Ginkgolide A, Parthenolides, Salicin, Eriodictyol, N-Acetyl-Cysteine, Magnesium, Zinc, Amentoflavone, Adiantum venestum, Amaranthus virdis, *Houttuynia cordata, Minthostachys mollis*, Sargassum fusiforme and *Usnea florida*.

According to still further features in the described preferred embodiments the dietary supplement having antagonistic activity against Dopamine D2 is selected from the group consisting of Limonene, Parthenolides, Eriodictyol, N-Acetyl-Cysteine, Alpha Lipoic Acid, Magnesium, Zinc, Amentoflavone, Adiantum venestum, Amaranthus virdis, *Houttuynia cordata, Minthostachys mollis*, Sargassum fusiforme and *Usnea florida*

According to still further features in the described preferred embodiments the dietary supplement having antagonistic activity against Dopamine D3 is selected from the group consisting of Ginkgolide C, Parthenolides, Eriodictyol, N-Acetyl-Cysteine, Magnesium, Zinc, Amentoflavone, Adiantum venestum, Amaranthus virdis, *Houttuynia cordata, Minthostachys mollis*, Sargassum fusiforme and *Usnea florida*.

According to still further features in the described preferred embodiments the dietary supplement having antagonistic activity against 5-HT1A is selected from the group consisting of Limonene, Proanthocyanidins and Zinc.

According to still further features in the described preferred embodiments the dietary supplement having antagonistic activity against 5-HT2 is selected from the group consisting of Puerarin, Limonene, Quercetin, Parthenolides, Salicin, Sulforaphane, Proanthocyanidins and Menthol.

According to still further features in the described preferred embodiments the dietary supplement having antagonistic activity against 5-HT3 is selected from the group consisting of Bilobalide, Ginkgolide B, Quercetin, Gingerols, Shogaols, Parthenolides, Proanthocyanidins and Menthol.

According to still further features in the described preferred embodiments the dietary supplement having agonistic activity against Glutamate is selected from the group consisting of Bilobalide, Huperzine A, N-Acetyl-Cysteine, Acetyl-L-Carnitine, Glutamic acid, Glycine, L-Glutamate, L-aspartate, L-Alanine, Magnesium and Zinc.

According to still further features in the described preferred embodiments the dietary supplement having agonistic activity against Adenosine A2A is selected from the group consisting of Polygala Limonene, Tenuifolia, Acorns gramineus, and *Poria cocos*.

According to still further features in the described preferred embodiments the dietary supplement having agonistic activity against 5-HT1B is selected from the group consisting of Limonene, Gingerols, Shogaols, Sulforaphane, Betaine and N-Acetyl-Cysteine.

According to still further features in the described preferred embodiments the dietary supplement having agonistic activity against 5-HT4 is selected from the group consisting of Mangiferin.

According to further features in the described embodiments, the dietary supplements having anti-gastroparesis, antiemetic, analgesic and anti-inflammatory activities are selected from the group having antagonistic activity against Dopamine D1, Dopamine D2, Dopamine D3, 5-HT3; and; agonistic activity against CB1, CB2, TRPA1, TRPV1, 5-HT4, and; further activity providing COX inhibition/suppression, Prostaglandin synthesis suppression, Histamine inhibition, AMPK upregulation and vascular spasm reduction.

According to still further features in the described preferred embodiments the dietary supplement having agonistic activity against CB1 and/or CB2 is selected from the group consisting of Cannabidiol and Falcarinol, According to still further features in the described preferred embodiments the dietary supplement having agonistic activity against TRPA1 is selected from the group consisting of Shogaols, Zinc, Mustard oil and Carnosol.

According to still further features in the described preferred embodiments the dietary supplement having agonistic activity against TRPV1 is selected from the group consisting of Shogaols, Piperin, Magnesium, Omega-3, Achinacea, Carvone and Camphor.

According to still further features in the described preferred embodiments the dietary supplement having Cox inhibitor activity is selected from the group consisting of Curcumin, Thunder God Vine, Resveratrol, Quercetin, Kaempferol, Pycogenol, Parthenolides, EGCG, Ursolic acid, Berberine and Ginsenosides.

According to still further features in the described preferred embodiments the dietary supplement having Prostaglandin inhibitor activity is selected from the group consisting of Gingerols, Shogaols, Salicin and Hesperidin.

According to still further features in the described preferred embodiments the dietary supplement having Histamine inhibitor activity is selected from the group consisting of Quercetin, Vitamin C, Mangosteen, and Butterbur.

According to further features in the described embodiments, the dietary supplements capable of increasing alcohol catabolism are selected from the group consisting of alcohol and acetaldehyde catabolism co-factors, acetate catabolism co-factors, an upregulator of ADH activity, an upregulator of ALDH activity, an upregulator of Cyp2E1 activity, an upregulator of NAD+ activity, an acetaldehyde binding agent, an upregulator or activator of AMPK and/or SIRT; and a down-regulator of CD38, CD157 and/or PARP.

According to still further features in the described preferred embodiments the dietary supplement is an Alcohol and/or Acetaldehyde catabolism co-factor selected from the group consisting of B Vitamins: 1,2,3,5,6,9 and 12, Pantethine, Vitamin E, TMG (Betaine), Choline salt, Zinc salt, SAMe, Nicotinamide, Folate/Folic acid and Alpha Lipoic Acid.

According to still further features in the described preferred embodiments the dietary supplement is an Acetate catabolism co-factor such as Co-enzyme A.

According to still further features in the described preferred embodiments the dietary supplement is an Acetaldehyde binding agent selected from the group consisting of Proanthocyanidins and Cysteinylglycine.

According to still further features in the described preferred embodiments the dietary supplement is an upregulator of ADH activity selected from the group consisting of Magnesium and Zinc.

According to still further features in the described preferred embodiments the dietary supplement is an upregulator of ALDH activity selected from the group consisting of Sulforaphane, N-Acetyl-Cysteine and Alpha Lipoic Acid.

According to still further features in the described preferred embodiments the dietary supplement is an upregulator of NAD+ activity selected from the group consisting of Resveratrol, Quercetin, Caffeine, Theophylline, Betaine/TMG, Choline, N-Acetyl-Cysteine, Alpha Lipoic Acid, Acetyl-L-Carnitine, Pyruvate, Co-Enzyme A and Fructose.

According to still further features in the described preferred embodiments the dietary supplement is an upregulator of AMPK activity selected from the group consisting of Bilobalide, Puerarin, Resveratrol, Quercetin, Shogaols, Salicin, Sulforaphane, Menthol, Betaine/TMG, Choline, Alpha Lipoic Acid and Acetyl-L-Carnitine.

According to still further features in the described preferred embodiments the dietary supplement is an upregulator of SIRT activity selected from the group consisting of Resveratrol, Quercetin, Curcumin, Sulforaphane, N-Acetyl-Cysteine and Fructose.

According to still further features in the described preferred embodiments the dietary supplement is a down-regulator of CD38 and/or CD157 activity selected from the group consisting of Quercetin.

According to still further features in the described preferred embodiments the dietary supplement is a down-regulator of PARP activity selected from the group consisting of Quercetin, Caffeine, Theophylline, Curcumin, Sulforaphane, Eriodictyol, Betaine/TMG, N-Acetyl-Cysteine and Pyruvate.

According to another aspect of the present invention there is provided an article of manufacturing comprising a container having two environmentally isolated compartments, a first compartment including the composition-of-matter of claim 1 and, a second compartment including a liquid, wherein at least a portion of the dietary supplements of (a), (b) and/or (c) are encapsulated within microparticles having a diameter of 25-100 microns.

According to still further features in the described preferred embodiments the container is constructed so as to enable mixing of the composition-of-matter with the liquid to generate a consumable suspension.

According to still further features in the described preferred embodiments the composition-of-matter includes Bilobalide, Dihydromyricetin (Ampelosin) Ginkgolides, Puerarin, Limonene, Huperzine, Gingerols, Shogaols, Salicinic acid, Parthenolides, Proanthocyanidins, Curcumin, Piperin, Quercetin, Sesamin, Mangiferin, Co-Enzyme A and/or Amentoflavone, According to still further features in the described preferred embodiments the Bilobalide, Dihydromyricetin (Ampelosin) Ginkgolides, Puerarin, Limonene, Huperzine, Gingerols, Shogaols, Salicin/Salicinic acid, Parthenolides, Proanthocyanidins, Curcumin, Piperin, Quercetin, Sesamin, Mangiferin, Co-Enzyme A and/or Amentoflavone, are microencapsulated.

According to still further features in the described preferred embodiments the microparticles include an encapsulant not soluble in acidic, enzyme-free liquid such as Zein and Shellac.

According to still further features in the described preferred embodiments the microparticles further include Shellac, HPMC, glycerol and/or talcum.

According to still further features in the described preferred embodiments the microparticles include Shellac, and at least one compound selected from the group consisting of HPMC, HPMCP, Zein, PVA, Carbomer 940, Methyl Cellulose, Ethyl Cellulose, Alginate, Whey, Casein, a plasticizer, (such as PEG, Triethyl Citrate and Glycerol) and Talc.

According to still further features in the described preferred embodiments the microparticles include one or a combination of Prolamin proteins (Zein, Wheat, etc.), Shellac, fats (Coconut oil, Palm oil), Gelatin, Soy proteins, Pea proteins (Globulin), Vegetable proteins, Dextran, Maltodextrin, Cyclodextrin, Whey, Caseine, Guar gum, gum Arabic, Pectin, Amylose, Starches, Guar gum, Pectins, Chitosans, Alginates, Hydrogels, Polymethacrylates, Ethyl Cellulose, Methyl Cellulose.

The present invention successfully addresses the shortcomings of the presently known configurations by providing a composition-of-matter that can be used to reduce or reverse both the physiological, motor and cognitive effects of alcohol on the body and/or deliver active ingredients to various regions of the GI in a timely manner.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
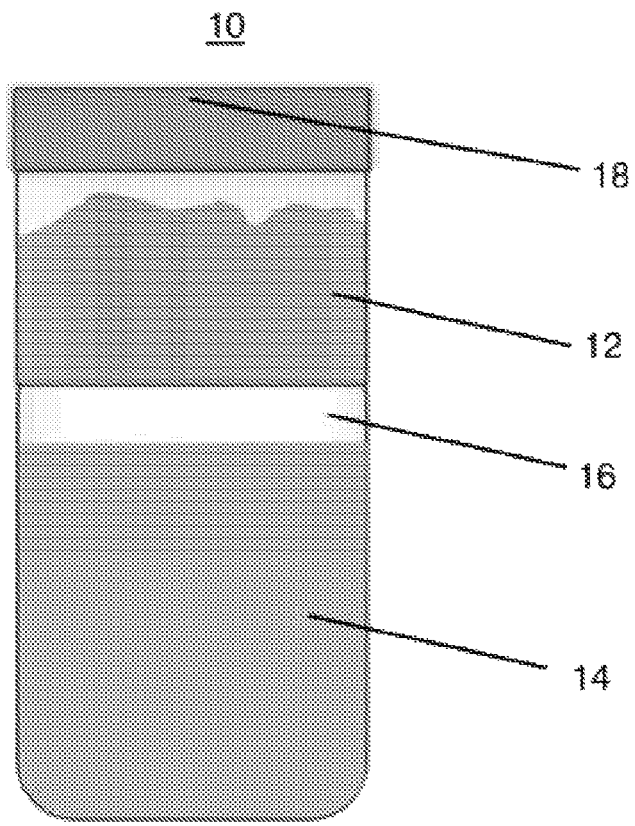
FIG. 1 illustrates a container suitable for delivery of the present composition.

The present invention is of a composition-of-matter which can be used to selectively deliver ingredients in the GI tract for the purpose of, for example, but not limited to, rapidly reversing or reducing the negative effects of alcohol consumption.

The principles and operation of the present invention may be better understood with reference to the drawings and accompanying descriptions and examples.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Several products attempt to provide relief from, or reduce the negative effects of alcohol consumption. Such products are unpopular with drinkers and do not provide the benefits claimed at least for the following reasons:

(i) people drink alcohol to enjoy its actual and/or perceived positive impacts: improved mood, social openness, etc. A product which is consumed prior to and/or concurrently with alcohol consumption, can reduce the desired effects of alcohol sought by drinkers.

(ii) due to solubility and bad taste issues, such products incorporate relatively small quantities (w/v or v/v) of active ingredients; such small quantities are not effective in timely coping with the dozens of milliliters of circulating pure alcohol and its metabolites.

(iii) compounds (vitamins, minerals, amino acids, etc.) depleted in the body during alcohol metabolism are water soluble (hydrophilic) and water insoluble (hydrophobic). Thus, replenishment of such compounds requires that both types of ingredients are present in a single liquid medium (for ensuring very quick availability in the GI tract). This results in a less than favorable consumption experience since some of the ingredients are present as a bad-tasting suspension;

(iv) some of the key compounds depleted from the body during alcohol metabolism are poorly absorbed through the intestines. As such, very little quantities of such ingredients are naturally absorbed into the blood stream from presently available products;

(v) some ingredients suitable for use in such products have an unpleasant taste and as such are often not used;

(vi) existing products do not address the negative effects of alcohol and its metabolites on cognitive functions such as information processing, memory, attention, concentration, decision making/impulse control, risk taking, and/or motor functions;

(vii) limited human data publically available for existing products demonstrates an alcohol metabolism acceleration of 5%-15%. This is relatively a low and insufficient acceleration outcome from a consumer standpoint.

(viii) existing products do not address the gastroparesis effects of alcohol consumption, which prevent or at the minimum significantly slow-down the passage of replenishing ingredients past the stomach and its absorption starting in the Duodenum.

(ix) Existing products do not address, sufficiently early, the negative physiological sensations resulting from alcohol consumption (e.g. nausea/vomiting, headache/migraine, stomach pain/abdominal pain, fatigue, etc.). As a result, instead of preventing the initiation of these symptoms, existing products target the reduction of symptoms after they have already occurred (typically the morning after).

(x) technologies for minimizing unpleasant taste primarily focus on taste masking. Taste masking can be effective in protection against a few hundred milligrams (at most) of bad tasting ingredients in a beverage or gel, but are ineffective when attempting to mask the bad tastes of ingredients at higher quantities.

While reducing the present invention to practice, the present inventors formulated a composition-of-matter that can be used to rapidly and timely remedy the variety of negative effects of alcohol consumption while addressing the above limitations of prior art products.

The present composition provides the following advantages:

(a) it can accelerate alcohol metabolism in the body by as much as 100%;

(b) it can effectively reduce the effect of alcohol on the brain, specifically the negative effects of alcohol on information processing, memory, cognition, decision making/impulse control, risk taking and motor performance;

(c) it can reduce the effect of alcohol on the body, specifically the negative effects of alcohol on physiology (e.g. nausea, vomiting, fatigue, headache, migraine, light headedness, stomach pain, abdominal pain, etc.);

(d) it can be consumed anytime following alcohol consumption while not negatively affecting the desired effect of alcohol as perceived by the consumer;

(e) it can provide effective quantities of the active ingredients in a relatively small volume of liquid, having a positive effect on the rate of response and effectiveness;

(f) it does not have an unpleasant taste or odor, even when the amount of ingredients is significant (between 10-100 grams);

(g) it can improve some of the negative effects of alcohol as early as 5-10 minutes post the beginning of consumption;

(h) it can prolong the duration of significant prevention or improvement of the alcohol intoxication symptoms to 2-8 hours post a single consumption;

(i) it is effective in treating both low blood alcohol levels (e.g. 0.020%-0.050%) as well as high blood alcohol levels (e.g. 0.050%-0.200%);

(j) It is effective in recovering gastrointestinal motility temporarily impaired by alcohol consumption;

(k) It is effective in recovering capabilities relating to information processing, memory, attention, decision making, impulse control, risk taking and motor performance impaired by alcohol consumption.

An embodiment of the composition-of matter of the present invention (also referred to herein as "the present composition") was formulated as a consumable liquid preparation and tested on intoxicated individuals. As is described in the Examples section which follows, consumption of the present composition following alcohol consumption led to recovery of gastrointestinal motility temporarily impaired by alcohol consumption, accelerated blood alcohol metabolism, facilitated quicker recovery of motor, cognitive, information processing, memory, concentration, attention, decision making, impulse control, risk taking mitigation capabilities; and; improved negative physiological sensations (e.g. nausea, vomiting, headache, migraine, stomach pain, abdominal pain, tiredness, exhaustion, etc.) resulting from excess alcohol consumption.

As used herein, excess alcohol consumption refers to an amount of alcohol that when consumed results in negative cognitive and/or physiological effects on the user. As used herein, "alcohol intoxication" or "excess alcohol consumption" refers to user's blood alcohol levels greater than 0.05%.

Thus, according to one aspect of the present invention there is provided a composition of matter which includes the following active ingredients:

(a) dietary supplements affecting motor and, cognitive performance;

(b) dietary supplements having anti-gastroparesis, antiemetic, analgesic and anti-inflammatory activities; and/or (c) dietary supplements being capable of increasing alcohol catabolism.

As used herein, a dietary supplement refers to a product taken orally that contains one or more ingredients that are intended to supplement an individual's diet and is not considered food (i.e. are not typically an energy source). Dietary supplements can be vitamins, minerals, herbs or other botanicals or extracts thereof, amino acids, or any other non-food substances capable of supplementing a diet. Carbohydrates which are typically used as an energy source, can also affect alcohol catabolism and are also optionally used in the present composition.

Although any of the above (a)-(c) can individually provide a beneficial effect on individuals under alcohol influence or intoxicated individuals, it will be appreciated that a composition-of-matter that includes (a) and (b), (a) and (c), (b) and (c) or (a)-(c) is preferred due to its combined effects.

Examples of dietary supplements of (a), (b) or (c) are described hereinbelow. A composition of matter that includes dietary supplements encompassing (a), (b) and (c) is exemplified by Table 8.

According to another aspect of the present invention there is provided a composition-of-matter which includes the following active ingredients:

(a) dietary supplements for reducing or abolishing the negative effects of alcohol on cognition, attention, concentration, memory, information processing, decision making, risk taking and/or impulse control, for example, supplements which exhibit antagonistic activity against GABA, dopamine, and serotonin and agonistic activity against glutamine;

(b) dietary supplements having free-radical scavenging, anti-gastroparesis, antiemetic, analgesic and anti-inflammatory activities; and/or (c) dietary supplements capable of increasing alcohol catabolism and/or reducing the levels of toxic products resulting from alcohol catabolism.

Although any of the above (a)-(c) can individually provide a beneficial effect on individuals under alcohol influence or intoxicated individuals, it will be appreciated that a composition-of-matter that includes (a) and (b), (a) and (c) or (b) and (c) or (a), (b) and (c) is presently preferred due to its combined effects.

A dietary supplement having antagonistic activity against GABA can be, for example, Bilobalide, Amentoflavone, Dihydromyricetin and Copper Glycinate Chelate. These exist in low concentrations in commercially available extracts of Ginkgo Biloba and Hovenia Dulcis, and its concentrations in extracts can be further elevated using commercially available extraction and purification technologies. i.e. Bilobalide, Amentoflavone, Dihydromyricetin can be sourced as a powdered extract from Ginkgo Biloba and Hovenia Dulcis while Copper Glycinate Chelate can be sourced as a Copper Glycinate Chelate from dietary supplement manufacturers.

A dietary supplement having agonistic activity against glutamate can be, for example, L-Glutamate, L-aspartate, L-Alanine, Magnesium and Zinc.

A dietary supplement having antagonistic activity against dopamine can be, for example, Amentoflavone, Adiantum venestum, Amaranthus virdis, *Houttuynia cordata, Minthostachys mollis*, Sargassum fusiforme and *Usnea florida*. Amentoflavone is present in different concentrations in Ginkgo Biloba extract. Extracts of Adiantum venestum, Amaranthus virdis, *Houttuynia cordata, Minthostachys mollis*, Sargassum fusiforme and *Usnea florida* are available from herbal extract manufacturers, primarily in China, India and South America.

A dietary supplement having antagonistic activity against serotonin can be, for example, Bilobalide, Ginkgolides, Gingerols, Ginsenosides, Amentoflavone and Puerarin. Bilobalide, Amentoflavone and Ginkgolides are present in different concentrations in extracts of Ginkgo Biloba. Gingerols are present in different concentrations in extracts from Ginger, Ginsenosides are present in different concentrations in extracts from differ varieties of Ginseng. Puerarin is present in different concentrations in extracts from Pueraria Lobata (Kudzu).

Dietary supplements that can increase alcohol breakdown in the body or that reduce the level of toxic products of catabolism include, for example, an upregulator of ADH activity, upregulator of ALDH1 activity, an upregulator of ALDH2 activity, an upregulator of Cyp2E1 activity, an upregulator of NAD+ activity, an acetaldehyde binding agent and an upregulator or activator of AMPK and/or SIRT.

A dietary supplement capable of increasing alcohol catabolism can be, for example, a B Vitamin (e.g. Vitamin B1, 2, 3, 5, 6, 9 and/or 12), Pantethine, Vitamin E, TMG (Betaine), Choline salt, Zinc salt, SAMe, Nicotinamide, Folate/Folic acid and Alpha Lipoic Acid.

Vitamin B6, Vitamin B12 and Folate can also be used as a Methionine metabolism recovery agent. Such an agent can reduce liver injury and circulating Homocysteine levels.

An example of an acetaldehyde binding agent can be Proanthocyanidins or Cysteinylglycine, while an upregulator or activator of AMPK and/or SIRT can be Resveratrol, Sulforaphane, Fructose and Curcumin. These ingredients can be sourced from grapes, Broccoli and Curcuma Longa from dietary supplement and plant extract manufacturers around the globe.

As is described hereinabove, the present composition can also include a dietary supplement having anti-gastroparesis, antiemetic, analgesic and/or anti-inflammatory activities.

An example of an antiemetic agent acting as a serotonin (5-HT) antagonist which can be used in the present composition is Proanthocyanidins, Gingerols, Ginsenosides, Bilobalide or Ginkgolides, an anti-Gatroparesis agent acting as TRPV1 agonist and/or TRPA1 agonist can be Eriodictyol, Ursolic Acid, Capsaicin, alpha-Spinasterol, Gingerols, Shogaols, MSG and Kiwi extract. Eriodictyol is present in a variety of concentrations in extracts of Yerba Santa. Capsaicin is present in a variety of concentrations in extracts of Peppers. Ursolic acid is present in a variety of different concentrations in extracts of Berries and Basil. Gingerols are present in a variety of concentrations in extracts of Ginger. Alpha-Spinasterol is present in a variety of concentrations in extracts of Spinach. MSG is available from a variety of food additive manufacturers.

The present composition can also include a lipid metabolism upregulating agent such as Creatine, Carnitine and Acetyl-L-Carnitine, as well as fish oil.

As is mentioned hereinabove, formulating a product capable of effectively reducing the variety of negative effects of excess alcohol consumption (also referred to herein as an "alcohol recovery product") is challenging due to two main problems: providing a functionally-effective amount of the active ingredients in a consumable product unit to facilitate a rapid and significant physiological effect, and, formulating the product such that the flavor and odor thereof are not unpleasant to the user.

The present inventors have addressed these issues by encapsulating some of the ingredients in microcapsules with different coatings which isolate, rather than mask, the odors and the flavors of unpleasant tasting and smelling active ingredients. Such microcapsules also enable loading of an effective amount of active ingredients in a liquid unit of several hundreds of milliliters, or in a gel. As is further described in the Examples section which follows, microencapsulation was also selected so as to minimize or negate the gritty oral sensation often accompanied with consumption of suspended powders. Such gritty oral sensation of a beverage or a gel is a major obstacle to obtain a satisfactory positive consumption experience by the user.

In addition, the present microencapsulation approaches were designed in order to selectively release different active ingredients (e.g. dietary supplements) throughout the GI tract (see the Examples section which follows for further description).

Several types of micro-encapsulation approaches can be used to encapsulate the dietary supplements of the present composition. Examples of such approaches include encapsulating the dietary supplement raw materials with enteric and/or other encapsulating materials in a fluidized bed; spray-drying a mixture of a dietary supplement and enteric/encapsulant ingredients; and/or; freeze-drying a mixture spray-drying a mixture of a dietary supplement and enteric/encapsulant ingredients, and then grinding it to the desired final particle size/diameter.

The Examples section which follows describes several approaches for encapsulating the dietary supplements of the present composition. The advantages of the technological approach is that given optimal parameters, it enables the generation of an effective isolative coating even in cases of very small particles of dietary supplements which are characterized by a foul taste and/or odor.

Dietary supplements which are preferably encapsulated include, but are not limited to, Alpha Lipoic Acid, Folic acid, Vitamin B1, Vitamin B2, Vitamin B3 (Nicotinamide), Vitamin B5/Pantethine, Vitamin B6, Vitamin B9 (Folate), Vitamin B12, Vitamin D, Vitamin E, Glutathione, Carnitine/Acetyl-L-Carnitine, Cysteine/N-Acetyl-Cysteine, Copper salt, Selenium salt, Magnesium salt, Zinc salt, Pyruvate salt, Co-enzyme A, Curcumin, Piperin, Quercetin, Resveratrol, Sesamin, Sulforaphane, Astaxanthin, Lemon (Limonene), Grape seed (Proanthocyanidins), Huperzia (Huperzine), Pueraria Lobata (Puerarin), Ginseng (Ginsenosides), Ginkgo Biloba (Bilobalide, Amentoflavone, Ginkgolides), Guarana (Caffeine, Theophylline), Ginger (Gingerols, Shogalos), Feverfew (Parthenolides), White Willow Bark (Salicylic acid), Mango (Mangiferin), Betaine (TMG), SAMe, Choline salt, Creatine, Fructose and Glucose.

Tables 1-14 below provide several exemplary compositions formulated according to the teachings of the present invention.

TABLE 1

| Dietary Supplement | Total (mg.) Low | Total (mg.) High |
|---|---|---|
| Alpha Lipoic Acid | 300 | 600 |
| Folic acid | 2.4 | 3.2 |
| Vitamin B1 | 500 | 500 |
| Vitamin B2 | 200 | 200 |
| Vitamin B3 (Nicotinamide) | 250 | 750 |
| Pantethine | 600 | 900 |
| Vitamin B6 | 200 | 200 |
| Vitamin B12 | 5 | 5 |
| Acetyl-L-Carnitine | 500 | 1,000 |
| N-Acetyl-Cysteine | 600 | 1,200 |
| Copper Glycinate Chelate | 2 | 2 |
| Selenium Chelate | 200 | 200 |
| Magnesium | 500 | 500 |
| Zinc Citrate | 50 | 50 |
| Vitamin E | 400 IU | 400 IU |
| Resveratrol | 250 | 500 |
| Sulphoraphane | 35 | 70 |
| Curcumin | 600 | 1,800 |
| Piperin | 60 | 90 |
| Fructose | 20,000 | 40,000 |
| Betaine (TMG) | 3,000 | 5,000 |
| Choline Bitratrate | 1,000 | 2,000 |
| Creatine | 1,000 | 2,000 |
| American Ginseng (Ginsenosides) | 300 | 900 |
| Ginkgo Biloba (Bilobalide, Ginkgolide B) | 300 | 600 |
| Hovenia Dulcis (Dihydromyricetin) | 250 | 1,000 |
| Pueraria Lobata (Puerarin) | 600 | 3,000 |
| Guarana extract | 600 | 1,200 |
| Glucose | 10,000 | 20,000 |
| Astaxanthin | 20 | 60 |
| Eriodictyol | 150 | 250 |
| Ginger extract (Gingerols, Shogaols) | 600 | 2,000 |
| Feverfew (Parathenolides) | 100 | 200 |
| White Willow Bark (Salicylic acid) | 120 | 240 |

TABLE 2

| Dietary Supplement | Total (mg.) Low | Total (mg.) High |
|---|---|---|
| Alpha Lipoic Acid | 300 | 600 |
| Folic acid | 2.4 | 3.2 |
| Vitamin B1 | 500 | 500 |

TABLE 2-continued

| Dietary Supplement | Total (mg.) Low | Total (mg.) High |
|---|---|---|
| Vitamin B2 | 200 | 200 |
| Vitamin B3 (Nicotinamide) | 250 | 750 |
| Pantethine | 600 | 900 |
| Vitamin B6 | 200 | 200 |
| Vitamin B12 | 5 | 5 |
| Acetyl-L-Carnitine | 500 | 1,000 |
| N-Acetyl-Cysteine | 600 | 1,200 |
| Copper Glycinate Chelate | 2 | 2 |
| Selenium Chelate | 200 | 200 |
| Magnesium | 500 | 500 |
| Zinc Citrate | 50 | 50 |
| Vitamin E | 400 IU | 400 IU |
| Resveratrol | 250 | 500 |
| Sulphoraphane | 35 | 70 |
| Curcumin | 600 | 1,800 |
| Piperin | 60 | 90 |
| Fructose | 20,000 | 40,000 |
| Betaine (TMG) | 3,000 | 5,000 |
| Choline Bitratrate | 1,000 | 2,000 |
| Creatine | 1,000 | 2,000 |
| American Ginseng (Ginsenosides) | 300 | 900 |
| Ginkgo Biloba (Bilobalide, Ginkgolide B) | 300 | 600 |
| Hovenia Dulcis (Dihydromyricetin) | 250 | 1,000 |
| Pueraria Lobata (Puerarin) | 600 | 3,000 |
| Guarana extract | 600 | 1,200 |
| Glucose | 10,000 | 20,000 |

TABLE 3

| Dietary Supplement | Total (mg.) Low | Total (mg.) High |
|---|---|---|
| Alpha Lipoic Acid | 300 | 600 |
| Folic acid | 2.4 | 3.2 |
| Vitamin B1 | 500 | 500 |
| Vitamin B2 | 200 | 200 |
| Vitamin B3 (Nicotinamide) | 250 | 750 |
| Pantethine | 600 | 900 |
| Vitamin B6 | 200 | 200 |
| Vitamin B12 | 5 | 5 |
| Acetyl-L-Carnitine | 500 | 1,000 |
| N-Acetyl-Cysteine | 600 | 1,200 |
| Copper Glycinate Chelate | 2 | 2 |
| Selenium Chelate | 200 | 200 |
| Magnesium | 500 | 500 |
| Zinc Citrate | 50 | 50 |
| Vitamin E | 400 IU | 400 IU |
| Resveratrol | 250 | 500 |
| Sulphoraphane | 35 | 70 |
| Curcumin | 600 | 1,800 |
| Piperin | 60 | 90 |
| Fructose | 20,000 | 40,000 |
| Betaine (TMG) | 3,000 | 5,000 |
| Choline Bitratrate | 1,000 | 2,000 |
| Creatine | 1,000 | 2,000 |
| Astaxanthin | 20 | 60 |
| Eriodictyol | 150 | 250 |
| Ginger extract (Gingerols, Shogaols) | 600 | 2,000 |
| Feverfew (Parathenolides) | 100 | 200 |
| White Willow Bark (Salicylic acid) | 120 | 240 |

TABLE 4

| Dietary Supplement | Total (mg.) Low | Total (mg.) High |
|---|---|---|
| Curcumin | 600 | 1,800 |
| Resveratrol | 250 | 500 |
| Piperin | 60 | 90 |
| American Ginseng (Ginsenosides) | 300 | 900 |
| Ginkgo Biloba (Bilobalide, Ginkgolide B) | 300 | 600 |
| Hovenia Dulcis (Dihydromyricetin) | 250 | 1,000 |
| Pueraria Lobata (Puerarin) | 600 | 3,000 |
| Guarana extract | 600 | 1,200 |
| Glocose | 10,000 | 20,000 |
| Astaxanthin | 20 | 60 |
| Eriodictyol | 150 | 250 |
| Ginger extract (Gingerols, Shogaols) | 600 | 2,000 |
| Feverfew (Parathenolides) | 100 | 200 |
| White Willow Bark (Salicylic acid) | 120 | 240 |

TABLE 5

| Dietary Supplement | Total (mg.) Low | Total (mg.) High |
|---|---|---|
| Alpha Lipoic Acid | 300 | 600 |
| Folic acid | 2.4 | 3.2 |
| Vitamin B1 | 500 | 500 |
| Vitamin B2 | 200 | 200 |
| Vitamin B3 (Nicotinamide) | 250 | 750 |
| Pantethine | 600 | 900 |
| Vitamin B6 | 200 | 200 |
| Vitamin B12 | 5 | 5 |
| Acetyl-L-Carnitine | 500 | 1,000 |
| N-Acetyl-Cysteine | 600 | 1,200 |
| Copper Glycinate Chelate | 2 | 2 |
| Selenium Chelate | 200 | 200 |
| Magnesium | 500 | 500 |
| Zinc Citrate | 50 | 50 |
| Vitamin E | 400 IU | 400 IU |
| Resveratrol | 250 | 500 |
| Sulphoraphane | 35 | 70 |
| Curcumin | 600 | 1,800 |
| Piperin | 60 | 90 |
| Fructose | 20,000 | 40,000 |
| Betaine (TMG) | 3,000 | 5,000 |
| Choline Bitratrate | 1,000 | 2,000 |
| Creatine | 1,000 | 2,000 |

TABLE 6

| Dietary Supplement | Total (mg.) Low | Total (mg.) High |
|---|---|---|
| Curcumin | 600 | 1,800 |
| Resveratrol | 250 | 500 |
| Piperin | 60 | 90 |
| American Ginseng (Ginsenosides) | 300 | 900 |
| Ginkgo Biloba (Bilobalide, Ginkgolide B) | 300 | 600 |
| Hovenia Dulcis (Dihydromyricetin) | 250 | 1,000 |
| Pueraria Lobata (Puerarin) | 600 | 3,000 |
| Guarana extract | 600 | 1,200 |
| Glocose | 10,000 | 20,000 |

TABLE 7

| Dietary Supplement | Total (mg.) Low | Total (mg.) High |
|---|---|---|
| Curcumin | 600 | 1,800 |
| Resveratrol | 250 | 500 |
| Piperin | 60 | 90 |
| Astaxanthin | 20 | 60 |
| Eriodictyol | 150 | 250 |
| Ginger extract (Gingerols, Shogaols) | 600 | 2,000 |
| Feverfew (Parathenolides) | 100 | 200 |
| White Willow Bark (Salicylic acid) | 120 | 240 |

TABLE 8

| Dietary Supplement | Total (mg.) Low | Total (mg.) High |
|---|---|---|
| Alpha Lipoic Acid | 300 | 600 |
| Vitamin B1 | 500 | 500 |
| Vitamin B2 | 200 | 200 |
| Vitamin B3 (Nicotinamide) | 250 | 750 |
| Vitamin B5 (Pantethine) | 600 | 900 |
| Vitamin B6 | 200 | 200 |
| Vitamin B9 (Folate) | 2.4 | 3.2 |
| Vitamin B12 | 5 | 5 |
| N-Acetyl-Cysteine | 600 | 1,200 |
| Magnesium oxide | 500 | 500 |
| Zinc Citrate | 50 | 50 |
| Vitamin D | 400 IU | 400 IU |
| Vitamin E | 400 IU | 400 IU |
| Calcium Pyruvate | 2,000 | 10,000 |
| Betaine (TMG) | 3,000 | 5,000 |
| Choline Bitratrate | 1,000 | 2,000 |
| Co-Enzyme A | 500 | 4,000 |
| Glutathione | 500 | 2,000 |
| Glucose | 10,000 | 20,000 |
| Quercetin | 500 | 1,500 |
| Curcumin | 600 | 1,800 |
| Piperin | 60 | 90 |
| Korean Ginseng (Ginsenosides) | 300 | 900 |
| Ginkgo Biloba (Bilobalide, Ginkgolides) | 300 | 600 |
| Pueraria Lobata (Puerarin) | 600 | 3,000 |
| Ginger extract (Gingerols, Shogaols) | 600 | 2,000 |
| Lemon extract (Limonene) | 500 | 1,500 |
| Huperzia extract (Huperzine) | 0.1 | 0.3 |
| Feverfew (Parthenolides) | 100 | 200 |
| White Willow Bark (Salicylic acid) | 120 | 240 |
| Grape seed extract (Proanthocyanidins) | 250 | 1,000 |
| Mango extract (Mangiferin) | 100 | 500 |

TABLE 9

| Dietary Supplement | Total (mg.) Low | Total (mg.) High |
|---|---|---|
| Alpha Lipoic Acid | 300 | 600 |
| Vitamin B1 | 500 | 500 |
| Vitamin B2 | 200 | 200 |
| Vitamin B3 (Nicotinamide) | 250 | 750 |
| Vitamin B5 (Pantethine) | 600 | 900 |
| Vitamin B6 | 200 | 200 |
| Vitamin B9 (Folate) | 2.4 | 3.2 |
| Vitamin B12 | 5 | 5 |
| N-Acetyl-Cysteine | 600 | 1,200 |
| Magnesium oxide | 500 | 500 |
| Zinc Citrate | 50 | 50 |
| Vitamin D | 400 IU | 400 IU |
| Vitamin E | 400 IU | 400 IU |
| Calcium Pyruvate | 2,000 | 10,000 |
| Betaine (TMG) | 3,000 | 5,000 |
| Choline Bitratrate | 1,000 | 2,000 |
| Co-Enzyme A | 500 | 4,000 |
| Glutathione | 500 | 2,000 |
| Glucose | 10,000 | 20,000 |
| Quercetin | 500 | 1,500 |
| Curcumin | 600 | 1,800 |
| Piperin | 60 | 90 |
| Korean Ginseng (Ginsenosides) | 300 | 900 |
| Ginkgo Biloba (Bilobalide, Ginkgolides) | 300 | 600 |
| Pueraria Lobata (Puerarin) | 600 | 3,000 |
| Ginger extract (Gingerols, Shogaols) | 600 | 2,000 |
| Lemon extract (Limonene) | 500 | 1,500 |
| Huperzia extract (Huperzine) | 0.1 | 0.3 |

TABLE 10

| Dietary Supplement | Total (mg.) Low | Total (mg.) High |
|---|---|---|
| Alpha Lipoic Acid | 300 | 600 |
| Vitamin B1 | 500 | 500 |
| Vitamin B2 | 200 | 200 |
| Vitamin B3 (Nicotinamide) | 250 | 750 |
| Vitamin B5 (Pantethine) | 600 | 900 |
| Vitamin B6 | 200 | 200 |
| Vitamin B9 (Folate) | 2.4 | 3.2 |
| Vitamin B12 | 5 | 5 |
| N-Acetyl-Cysteine | 600 | 1,200 |
| Magnesium oxide | 500 | 500 |
| Zinc Citrate | 50 | 50 |
| Vitamin D | 400 IU | 400 IU |
| Vitamin E | 400 IU | 400 IU |
| Calcium Pyruvate | 2,000 | 10,000 |
| Betaine (TMG) | 3,000 | 5,000 |
| Choline Bitratrate | 1,000 | 2,000 |
| Co-Enzyme A | 500 | 4,000 |
| Glutathione | 500 | 2,000 |
| Glucose | 10,000 | 20,000 |
| Quercetin | 500 | 1,500 |
| Curcumin | 600 | 1,800 |
| Piperin | 60 | 90 |
| Feverfew (Parthenolides) | 100 | 200 |
| White Willow Bark (Salicylic acid) | 120 | 240 |
| Grape seed extract (Proanthocyanidins) | 250 | 1,000 |
| Mango extract (Mangiferin) | 100 | 500 |

TABLE 11

| Dietary Supplement | Total (mg.) Low | Total (mg.) High |
|---|---|---|
| Quercetin | 500 | 1,500 |
| Curcumin | 600 | 1,800 |
| Piperin | 60 | 90 |
| Korean Ginseng (Ginsenosides) | 300 | 900 |
| Ginkgo Biloba (Bilobalide, Ginkgolides) | 300 | 600 |
| Pueraria Lobata (Puerarin) | 600 | 3,000 |
| Ginger extract (Gingerols, Shogaols) | 600 | 2,000 |
| Lemon extract (Limonene) | 500 | 1,500 |
| Huperzia extract (Huperzine) | 0.1 | 0.3 |
| Feverfew (Parthenolides) | 100 | 200 |
| White Willow Bark (Salicylic acid) | 120 | 240 |
| Grape seed extract (Proanthocyanidins) | 250 | 1,000 |
| Mango extract (Mangiferin) | 100 | 500 |

TABLE 12

| Dietary Supplement | Total (mg.) Low | Total (mg.) High |
|---|---|---|
| Alpha Lipoic Acid | 300 | 600 |
| Vitamin B1 | 500 | 500 |
| Vitamin B2 | 200 | 200 |
| Vitamin B3 (Nicotinamide) | 250 | 750 |
| Vitamin B5 (Pantethine) | 600 | 900 |
| Vitamin B6 | 200 | 200 |
| Vitamin B9 (Folate) | 2.4 | 3.2 |
| Vitamin B12 | 5 | 5 |
| N-Acetyl-Cysteine | 600 | 1,200 |
| Magnesium oxide | 500 | 500 |
| Zinc Citrate | 50 | 50 |
| Vitamin D | 400 IU | 400 IU |
| Vitamin E | 400 IU | 400 IU |
| Calcium Pyruvate | 2,000 | 10,000 |
| Betaine (TMG) | 3,000 | 5,000 |
| Choline Bitratrate | 1,000 | 2,000 |
| Co-Enzyme A | 500 | 4,000 |
| Glutathione | 500 | 2,000 |
| Glucose | 10,000 | 20,000 |
| Quercetin | 500 | 1,500 |

TABLE 12-continued

| Dietary Supplement | Total (mg.) Low | Total (mg.) High |
|---|---|---|
| Curcumin | 600 | 1,800 |
| Piperin | 60 | 90 |

TABLE 13

| Dietary Supplement | Total (mg.) Low | Total (mg.) High |
|---|---|---|
| Quercetin | 500 | 1,500 |
| Curcumin | 600 | 1,800 |
| Piperin | 60 | 90 |
| Korean Ginseng (Ginsenosides) | 300 | 900 |
| Ginkgo Biloba (Bilobalide, Ginkgolides) | 300 | 600 |
| Pueraria Lobata (Puerarin) | 600 | 3,000 |
| Ginger extract (Gingerols, Shogaols) | 600 | 2,000 |
| Lemon extract (Limonene) | 500 | 1,500 |
| Huperzia extract (Huperzine) | 0.1 | 0.3 |

TABLE 14

| Dietary Supplement | Total (mg.) Low | Total (mg.) High |
|---|---|---|
| Feverfew (Parthenolides) | 100 | 200 |
| White Willow Bark (Salicylic acid) | 120 | 240 |
| Grape seed extract (Proanthocyanidins) | 250 | 1,000 |
| Mango extract (Mangiferin) | 100 | 500 |

The composition-of-matter of the present invention can be formulated into any consumable product including gels, bars, snacks, shakes or drinks. The composition-of-matter of the present invention is optimized, and thus has significant benefits, when delivered in a water-containing formulation as a suspension or dispersion.

Microencapsulation is a technology that is used to protect ingredients from degradation due to heat, moisture and/or presence of oxygen. Microencapsulation is also used to mask bad odors and tastes of ingredients and to enable controlled and targeted release/delivery of active ingredients in the GI tract.

The present invention utilizes microencapsulation to isolate the taste and organoleptic characteristic (mouth sensation of particles) of various active ingredients and to deliver ingredients to different target sites in the GI tract.

The microencapsulated active ingredients are formulated as a powder which can be dispersed in a liquid beverage, shake or gelprior to consumption.

The powder can be manufactured via spray drying with a three fluid or four fluid injectors incorporating more than a single fluid nozzle and capable of generating, in a single step, a core containing the active ingredient surrounded by at least one layer of a coating made from, for example, cellulose derivatives, proteins, methacrylate and other coating materials known in the food and pharmaceutical industry. Suitable spray drying technologies for use with the present invention include, but not limited to, 3-fluid spray drying, 4-fluid spray drying and ultrasonic dual-fluid or ultrasonic triple-fluid spray drying.

The final microencapsulated product is a powder that is dispersed into, an acidic (2.0-4.0) liquid beverage, shake or a gel.

Since the powder is insoluble and includes a high dose of active ingredients, a particle size optimizing dispersion, loading and minimization of a negative mouth sensation (organoleptic) was selected. The present inventors uncovered that a particle diameter for optimizing between particle loading and positive organoleptic sensation ranges between 20-100 microns, with 45-75 microns being the preferred size for the aforementioned application.

Suspended particles in liquid with a diameter above 100 microns produce an unpleasant sand-like gritty sensation in the mouth. Human experiments conducted by the present inventors uncovered that particles having a diameter of 15 to 100 microns do not produce such a sensation. In contrast, particles with a diameter of 120 microns or higher, typical to the minimum diameter provided by fluidized bed coating, generate a very unpleasant gritty, sand-like sensation in the mouth.

Thus, an optimal diameter for a microparticle is between 25-100 microns and preferably between 45-75 microns. A diameter of 45-75 microns optimizes between minimum coating loading and a positive oral sensation (and thus an overall positive consumption experience) of a consumer. The ratio of core to coating (w/w) is between 1:10 to 20:1, preferably in the range between 2:1 to 5:1.

The microparticles are coated so as to be nearly insoluble in the aqueous environment of the consumed product, and in the mouth and esophagus of the individual consuming it.

As is described in Example 6 below, the powder composition can include several types of particles each offering a different release trigger and a different profile of release of the active ingredient core in the GI tract (stomach and below).

Such selective release can be effected using different types of coating layers that are pH independent, and its disintegration is triggered in presence of enzymes, and augmented mechanical GI tract forces For example, coatings that are insoluble in non-enzymatic acidic conditions can be fabricated from coating compositions based on Prolamin proteins (Zein, Wheat, etc.), Shellac, fats (Coconut oil, Palm oil, etc.), and any combination thereof. Such coatings can be used to selectively release the active core.

Coatings dissolution in the presence of specific digestive enzymes can be based on Gelatin, Soy proteins, Pea proteins (Globulin), Vegetable proteins, fats, Starches, Dextran, Maltodextrin, Cyclodextrin, Whey and Caseine, and any combination thereof. Such coatings can be used to release the active core of the micro particle in the stomach.

Coatings dissolution in the presence of a specific digestive enzyme of the small intestines include, but not limited to: Guar gum, gum Arabic, Pectin and Amylose, and any combination thereof. Such coatings can be used to release the active core of the microparticle in the small intestine.

Coatings dissolution in the presence of enzyme of the colon include, but not limited to, Starches, Guar gum, Pectins, Chitosans, Alginates, Hydrogels, and any combination thereof. Such coatings can be used to release the active core of the microparticle in the Colon.

Coatings dissolution under low pH conditions include, but not limited to, Polymethacrylates. Such coatings can be used to release the active core of the microparticle in the stomach.

Other coatings that facilitate slow-release/controlled release, independent of enzymatic and pH conditions include, but not limited to, Ethyl Cellulose. Such coatings can be used for controlled release of an active core throughout the GI tract. water-soluble coatings include, but not limited to, Methyl Cellulose. Such coatings can be used in combination with the coatings described above in order to accelerate dissolution under the aforementioned conditions.

The encapsulating layer of the microparticles can be non-uniform to allow selective dissolution of the microparticles and prolonged selective release of the active ingredient. Several approaches for enabling selective release of active ingredients from coated microparticles are described in the Examples section which follows.

When the encapsulated microparticles are reconstituted into a liquid-based composition, the microparticles are preferably suspended in the liquid and are homogenously distributed therein (e.g. not floating at the surface of the liquid and not settling at the bottom of the container).

The encapsulated microparticles are inert or materially inert in as far as taste and odor, or, incorporate a flavoring agent which masks or at the minimum materially masks the taste of the encapsulating coating layer. Following contact with the liquid, the encapsulation coating layer of the dietary supplement is designed not to dissolve or breakdown (e.g. to release its active core content) in the acidic non-enzymatic conditions of the liquid or the gel for at least 20 minutes. This enables the microparticles to survive as a suspension in the liquid/gel and pass through the mouth and esophagus without substantially releasing its contents. Once passed the esophagus, the composition begins to release its active ingredients (in a selective and controlled manner) in the stomach and/or the small intestines and/or in the colon, depending on the viscosity of the carrier, the properties of the coating layer and the (w/w) ratio between the encapsulation material and active ingredients.

As is mentioned hereinabove, the present composition can include more than one type of a micro particle in a single powdered product. Different types of microparticles can include different cores (i.e. different active ingredient) and/or a different type of coating (facilitating selective release of more than one active ingredient).

For example, a single powdered dose unit can include:
(a) a microparticle facilitating rapid release of ingredient X (a dietary supplement) in the stomach
(b) a microparticle facilitating delayed release of ingredient Y (a dietary supplement) in the intestines (delay of 15-120 minutes post consumption); and
(c) a microparticle facilitating delayed release of (a dietary supplement) ingredient Z in the colon along (delay of 15-480 minutes post consumption).

Each micro-particle has a core with at least one active ingredient. The active ingredient of the core can be mononuclear, multi-nuclear or incorporated in a slow-release or controlled release matrix. The core can also incorporate intestinal permeability enhancing agents.

Each microparticle can include more than one coating layer, e.g. two or more coating layers each having a different dissolvability profile.

A single coating layer is intended for use in beverages or other reconstituted compositions having a high-water content. A single layer of coating is designed to prevent the release of foul-tasting ingredients into the water for a time period sufficient for a common consumer to completely consume a 330-500 ml serving, e.g. 20-30 minutes.

A single encapsulation layer incorporating at least 2 coating materials each having a different dissolvability profiles can be used to obtain stepwise release profiles.

The microencapsulated active ingredients of the present invention can also be provided in a Ready-To-Drink (RTD) beverage. In order to provide a reasonable shelf-life for the RTD version, more than a single encapsulation coating layer is required. A first (and inner) encapsulation coating layer can control release as described above and at least one additional encapsulation layer can be used to seal the core and 1st encapsulation layer from the water in the RTD product. Such an outer encapsulation coating layer is designed for maximum sealing, and is rapidly breached under the enzymatic and/or mechanical grinding conditions of the stomach thereby exposing the inner encapsulation layer and its selective dissolution thereof.

The outer (second) encapsulation coating layer can include materials which are insoluble in acidic, non-enzymatic conditions, but are rapidly dissolved/disintegrated under the enzymatic and/or mechanical grinding conditions of the stomach. Such materials include, but not limited to, Prolamin proteins (Zein, Wheat, etc.) and fats (Coconut oil, Palm oil) and any combinations thereof.

Table 15 below describes release profiles of several types of products.

TABLE 15 release profiles of various powders

| | Release In Beverage/ Gel Media | Release In Mouth | Release In Esophagus | Release In Stomach | Controlled Release In Small Intestines | Controlled Release In Colon |
|---|---|---|---|---|---|---|
| Alcohol Metabolism Acceleration | 0%-5% | 0%-2% | 0%-2% | 1%-33% | 66%-95% | 1%-33% |
| | Glutathione | Glutathione | Glutathione | Glutathione | Glutathione | Glutathione |
| | ALA | ALA | ALA | ALA | ALA | ALA |
| | Vitamin B1 | Vitamin B1 | Vitamin B1 | Vitamin B1 | Vitamin B1 | Vitamin B1 |
| | Vitamin B2 | Vitamin B2 | Vitamin B2 | Vitamin B2 | Vitamin B2 | Vitamin B2 |
| | Vitamin B3 | Vitamin B3 | Vitamin B3 | Vitamin B3 | Vitamin B3 | Vitamin B3 |
| | Vitamin B5 | Vitamin B5 | Vitamin B5 | Vitamin B5 | Vitamin B5 | Vitamin B5 |
| | Vitamin B6 | Vitamin B6 | Vitamin B6 | Vitamin B6 | Vitamin B6 | Vitamin B6 |
| | Vitamin B9 | Vitamin B9 | Vitamin B9 | Vitamin B9 | Vitamin B9 | Vitamin B9 |
| | Vitamin B12 | Vitamin B12 | Vitamin B12 | Vitamin B12 | Vitamin B12 | Vitamin B12 |
| | Vitamin D | Vitamin D | Vitamin D | Vitamin D | Vitamin D | Vitamin D |
| | Vitamin E | Vitamin E | Vitamin E | Vitamin E | Vitamin E | Vitamin E |
| | Coenzyme A | Coenzyme A | Coenzyme A | Coenzyme A | Coenzyme A | Coenzyme A |
| | Acetyl-L-Carnitine | Acetyl-L-Carnitine | Acetyl-L-Carnitine | Acetyl-L-Carnitine | Acetyl-L-Carnitine | Acetyl-L-Carnitine |
| | NAC | NAC | NAC | NAC | NAC | NAC |
| | Magnesium | Magnesium | Magnesium | Magnesium | Magnesium | Magnesium |
| | Zinc | Zinc | Zinc | Zinc | Zinc | Zinc |
| | Quercetin | Quercetin | Quercetin | Quercetin | Quercetin | Quercetin |
| | Resveratrol | Resveratrol | Resveratrol | Resveratrol | Resveratrol | Resveratrol |
| | Sulforaphane | Sulforaphane | Sulforaphane | Sulforaphane | Sulforaphane | Sulforaphane |

TABLE 15-continued release profiles of various powders

|  | Release In Beverage/ Gel Media | Release In Mouth | Release In Esophagus | Release In Stomach | Controlled Release In Small Intestines | Controlled Release In Colon |
|---|---|---|---|---|---|---|
| Cognitive & motor Performance Recovery | Betaine/TMG Choline Glucose 0%-5% Ginkgo extract (Bilobalide, Gikgolides) Kudzu extract (Puerarin) Lemon extract (Limonene) Huperzia extract (Huperzine) Ginseng extract (Ginsenosides) | Betaine/TMG Choline Glucose 0%-2% Ginkgo extract (Bilobalide, Gikgolides) Kudzu extract (Puerarin) Lemon extract (Limonene) Huperzia extract (Huperzine) Ginseng extract (Ginsenosides) | Betaine/TMG Choline Glucose 0%-2% Ginkgo extract (Bilobalide, Gikgolides) Kudzu extract (Puerarin) Lemon extract (Limonene) Huperzia extract (Huperzine) Ginseng extract (Ginsenosides) | Betaine/TMG Choline Glucose 1%-33% Ginkgo extract (Bilobalide, Gikgolides) Kudzu extract (Puerarin) Lemon extract (Limonene) Huperzia extract (Huperzine) Ginseng extract (Ginsenosides) | Betaine/TMG Choline Glucose 66%-95% Ginkgo extract (Bilobalide, Gikgolides) Kudzu extract (Puerarin) Lemon extract (Limonene) Huperzia extract (Huperzine) Ginseng extract (Ginsenosides) | Betaine/TMG Choline Glucose 1%-33% Ginkgo extract (Bilobalide, Gikgolides) Kudzu extract (Puerarin) Lemon extract (Limonene) Huperzia extract (Huperzine) Ginseng extract (Ginsenosides) |
| Nausea, pain & physiological discomfort reduction | Curcumin 0%-5% Grape seed extract (Proantho-cyanidins) Feverfew (Parthenolides) Ginger (Gingerols & Shogaols) | Curcumin 0%-2% Grape seed extract (Proantho-cyanidins) Feverfew (Parthenolides) Ginger (Gingerols & Shogaols) | Curcumin 0%-2% Grape seed extract (Proantho-cyanidins) Feverfew (Parthenolides) Ginger (Gingerols & Shogaols) | Curcumin 1%-20% Grape seed extract (Proantho-cyanidins) Feverfew (Parthenolides) Ginger (Gingerols & Shogaols) | Curcumin 20%-80% White Willow Bark extract (Salicin) Grape seed extract (Proantho-cyanidins) Feverfew (Parthenolides) Ginger (Gingerols & Shogaols) | Curcumin 20%-80% White Willow Bark extract (Salicin) Grape seed extract (Proantho-cyanidins) Feverfew (Parthenolides) Ginger (Gingerols & Shogaols) |
| Gastric motility recovery | 0%-5% Mango extract (Mangiferin) Piperin | 0%-2% Mango extract (Mangiferin) Piperin | 0%-2% Mango extract (Mangiferin) Piperin | 33%-66% Mango extract (Mangiferin) Piperin | 33%-66% Mango extract (Mangiferin) Piperin | 0%-2%% Mango extract (Mangiferin) Piperin |

The composition-of-matter of the present invention can be formulated as a ready-to-consume water-based drink, shake or gel which includes any of the above described ingredients as well as colorants, thickeners, flavoring agents, stabilizers and the like, or, as a powder containing the microencapsulated microparticles to be reconstituted in a drink or a gel prior to its consumption.

A composition-of-matter formulated as a drink is also served in a container which maintains at least some of the active ingredients in powder form and isolated from the liquid carrier.

Thus, according to another aspect of the present invention, there is provided an article of manufacturing which includes a container having two environmentally isolated compartments, one compartment for containing active ingredients in powder form, and the other for containing water and optionally dissolved components such as Fructose, Glucose, Betaine, Choline salt, and Creatine.

FIG. 1 illustrates one such container which is referred to herein as container 10. Container 10 is preferably shaped as elongated cylinder 25 cm in height, 6.5 cm in diameter and having a volume of 300-700 ml. Container 10 can be fabricated from, but not limited to, PET or Polypropylene using well known approaches. Container 10 includes two, environmentally-isolated, compartments (12 and 14) which are separated by partition 16. Container 10 further includes an opening 18 for accessing the contents of container 10, opening 18 can be sealed via a single use cover such as a pull tab, or a multi-use cover such as a screw cap. First compartment 12 is designed for containing the composition-of-matter described herein (e.g. the active ingredients of Table 2), while second compartment 14 is designed for containing the liquid carrier (water, optionally with dissolved components). Container 10 is designed such that partition 16 is breachable prior to unsealing of opening 18 thus enabling a user to mix the components of compartment 12 with the liquid of compartment 14 prior to consumption.

Partition 16 can be breached via one of several mechanisms which can be functionally connected to a lid or cap covering opening 18. For example, a screw cap covering opening 18 can be physically connected to partition 16 such that unscrewing of the screw cap breaches partition 18.

In any case, once wall 16 is breached by the user, the container can be vigorously shaken in order to dissolve and/or suspend the active ingredients in the water prior to consumption.

Thus, the present invention provides a composition-of-matter which can be used to counteract the negative effects of alcohol consumption in a rapid and timely manner.

The composition of the present invention concurrently and timely addresses three key aspects of excess alcohol consumption by providing effective alcohol catabolism, improvements in motor, cognitive, attention, task switching, quality decision making and reduced risk taking behavior; and improvements in physiological sensations/feeling. Since the present composition can include relatively large quantities of water it also provides a beneficial rehydration effect along with large quantities of active ingredients.

The present composition was designed for consumption following (e.g. after) alcohol uptake so as to not influence the desired positive effects of alcohol consumption from the consumer's subjective perception. However, consumption of the present composition prior to and/or concurrently with, alcohol consumption, would prevent blood alcohol levels from peaking and thus would prevent or at least reduce motor and cognitive performance from degrading.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non limiting fashion.

Example 1

Encapsulation of Glucose

Glucose with a pre-encapsulation diameter of 25 microns was encapsulated with a shellac-based composition. The shellac encapsulate included 65 grams of Shellac (SSB 57), 15 grams of Glycerin, 20 grams of HPMC (Vivapur E5LV), 3 grams of talcum and 600 grams of water.

A fluidized bed was used for encapsulating the Glucose under the following conditions: Pressure blow back: 1.3-2.1 [bar]; Pressure pump feed: 3.4 [bar]; Spraying pressure: 2.5 [bar]; Airflow: 3.0 [$M^3$ per second]; Air temperature: 40 [Celsius].

150 grams of Glucose and 75 grams of the Shellac-based composition (50% encapsulation) were processed via 7 cycles of the following: 108 seconds of mixing with the encapsulation composition+600 seconds of drying the encapsulated Glucose without additional free encapsulate.

Figure 2:
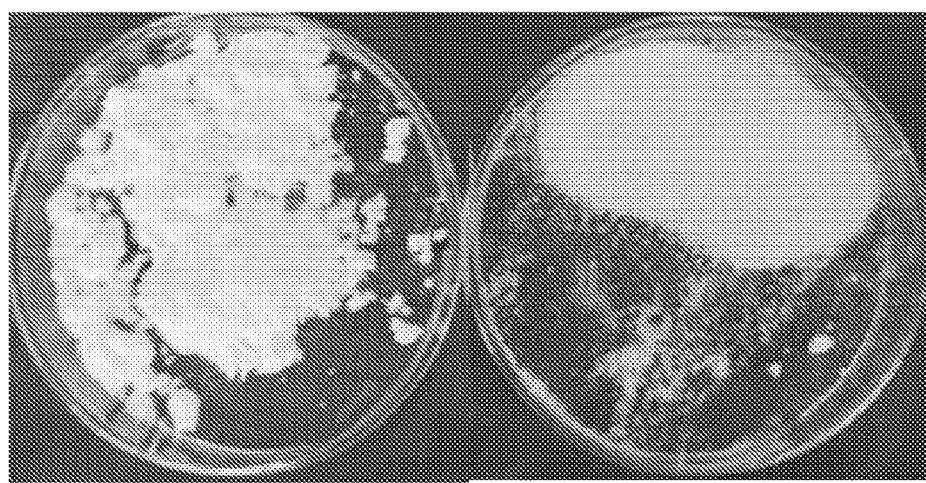
FIG. 2 illustrates non-encapsulated Glucose (left image) and Shellac-based encapsulated Glucose (right image).

FIG. 2 illustrates the non-encapsulated Glucose (left image) and Shellac-based encapsulated Glucose (right image).

Encapsulated Glucose was placed under conditions simulating the stomach (pH 1.2) for 30 minutes, and then under conditions simulating the small intestines (pH 6.8). A D-Glucose UV Test (R-Biopharm) was used to analyze the quantity of Glucose released to the surrounding media. Following 30 minutes at pH 1.2 (stomach), 10% of the Glucose was released to the surrounding media. At pH 6.8 (intestines), all the remaining Glucose was released to the surrounding media following 40 minutes.

Example 2

Accelerating Alcohol Catabolism in Human Subjects

A study on 19 participants (9 males and 10 females, ages 21-29), evaluated the increase in alcohol catabolism between control (no dietary supplements) and study arm (with the composition of matter) after each of the participants consumed 500 cc of beer with 4.9% alcohol (e.g. 24.5 cc of pure alcohol). Table 16 below summarizes the findings.

TABLE 16

| # | Gender | Blood Volume | Control 30 m-End BAC %/h | Composition 30 m-End BAC %/h | Diff BAC %/h 30 m-End (%) |
|---|---|---|---|---|---|
| 1 | M | 6,160 | 0.015% | 0.027% | 79% |
| 2 | M | 5,313 | 0.012% | 0.021% | 80% |
| 3 | F | 3,243 | 0.017% | 0.018% | 7% |
| 4 | F | 4,221 | 0.009% | 0.016% | 81% |
| 5 | M | 5,498 | 0.011% | 0.015% | 31% |
| 6 | M | 6,391 | 0.011% | 0.016% | 46% |
| 7 | F | 4,134 | 0.009% | 0.015% | 62% |
| 8 | F | 3,685 | 0.019% | 0.022% | 18% |
| 9 | F | 4,020 | 0.018% | 0.029% | 63% |
| 10 | M | 4,620 | 0.014% | 0.018% | 35% |
| 11 | M | 5,082 | 0.011% | 0.019% | 66% |
| 12 | F | 4,221 | 0.018% | 0.022% | 25% |
| 13 | F | 3,450 | 0.013% | 0.019% | 47% |
| 14 | M | 4,620 | 0.010% | 0.015% | 48% |
| 15 | M | 5,621 | 0.011% | 0.023% | 101% |
| 16 | F | 5,226 | 0.013% | 0.022% | 71% |
| 17 | F | 3,685 | 0.017% | 0.017% | 0% |
| 18 | F | 3,685 | 0.012% | 0.014% | 22% |
| 19 | M | 4,312 | 0.015% | 0.019% | 31% |
| 20 | | | | | |
| General | | | | | |
| Average | | | 0.013% | 0.019% | 48% |
| Median | | | 0.013% | 0.019% | 47% |
| SD | | | 0.003% | 0.004% | 28% |
| P-value | | | | 0.00000 | |
| Males | | | | | |
| Average | | | 0.012% | 0.019% | 57% |
| Median | | | 0.011% | 0.019% | 48% |
| SD | | | 0.002% | 0.004% | 25% |
| Females | | | | | |
| Average | | | 0.015% | 0.019% | 40% |
| Median | | | 0.015% | 0.019% | 36% |
| SD | | | 0.004% | 0.004% | 29% |

The median alcohol catabolism rate was 0.019%/h in the composition-treated individuals vs. 0.013%/h in the control army, a 47% advantage (p=0.00000). In men, the median alcohol catabolism rate was 0.019%/h in the composition-treated individuals vs. 0.011%/h in the control arm, a 48% advantage. In women, the median alcohol catabolism rate in the composition study was 0.019%/h in the composition-treated individuals vs. 0.015%/h in the control arm, a 36% advantage.

Example 3

Increasing Motor and Cognitive Performance in Human Subjects

A 53 years old male, who does not frequently consume alcohol and weighs 85 kg, fasted for 2 hours prior to consuming 59 grams of alcohol (71 cc of 96% alcohol) admixed with 160 cc of Cold Forrest berries' juice. It took the individual 20 minutes to consume the liquid. Twenty minutes following consumption, the participant consumed a composition of matter which included dietary supplements selected for improving motor and cognitive functions.

Figure 3:
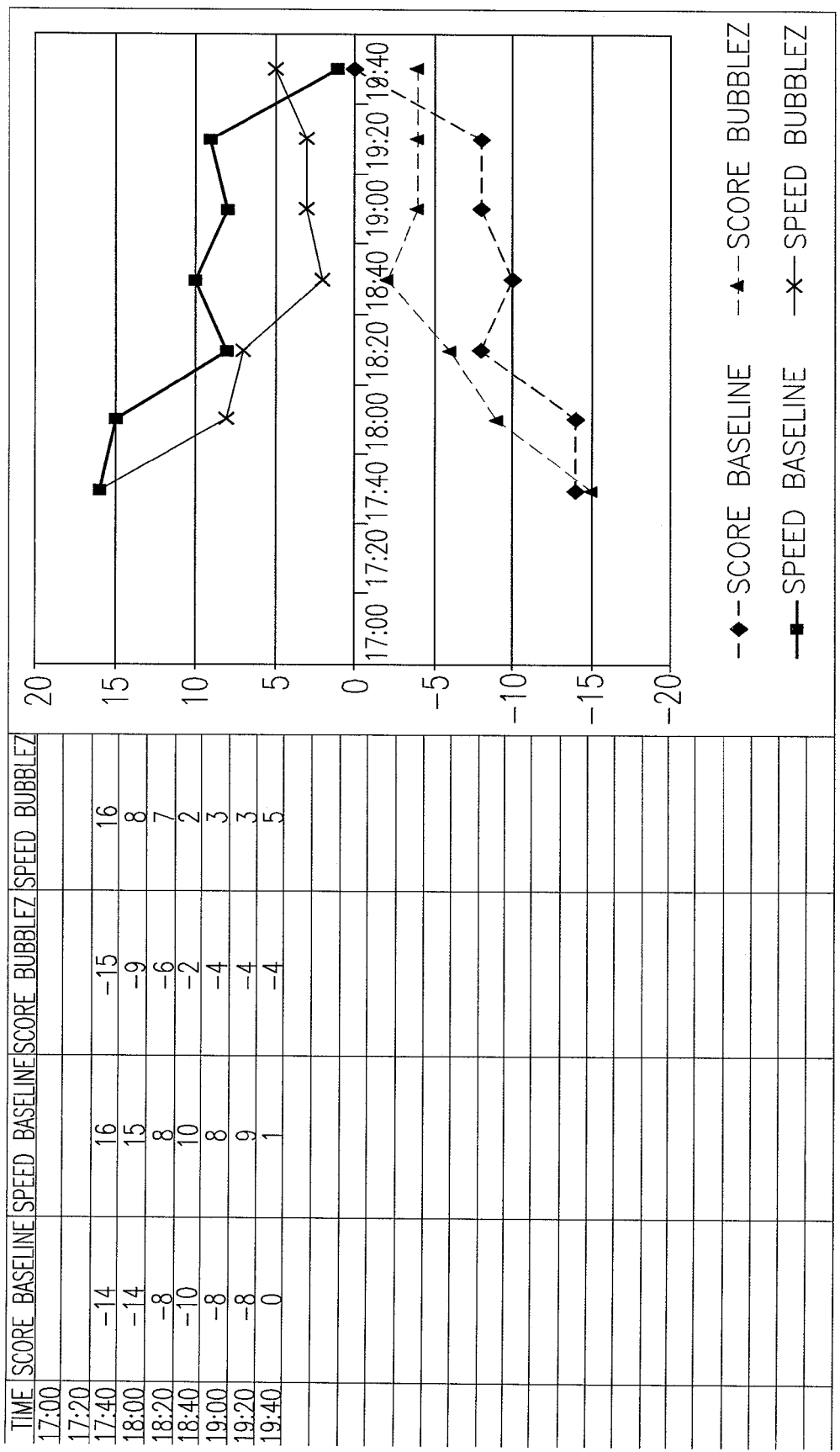
FIGS. 3-6 illustrate the effect of the present composition on the motor and cognitive functions of an intoxicated subject.
Figure 4:
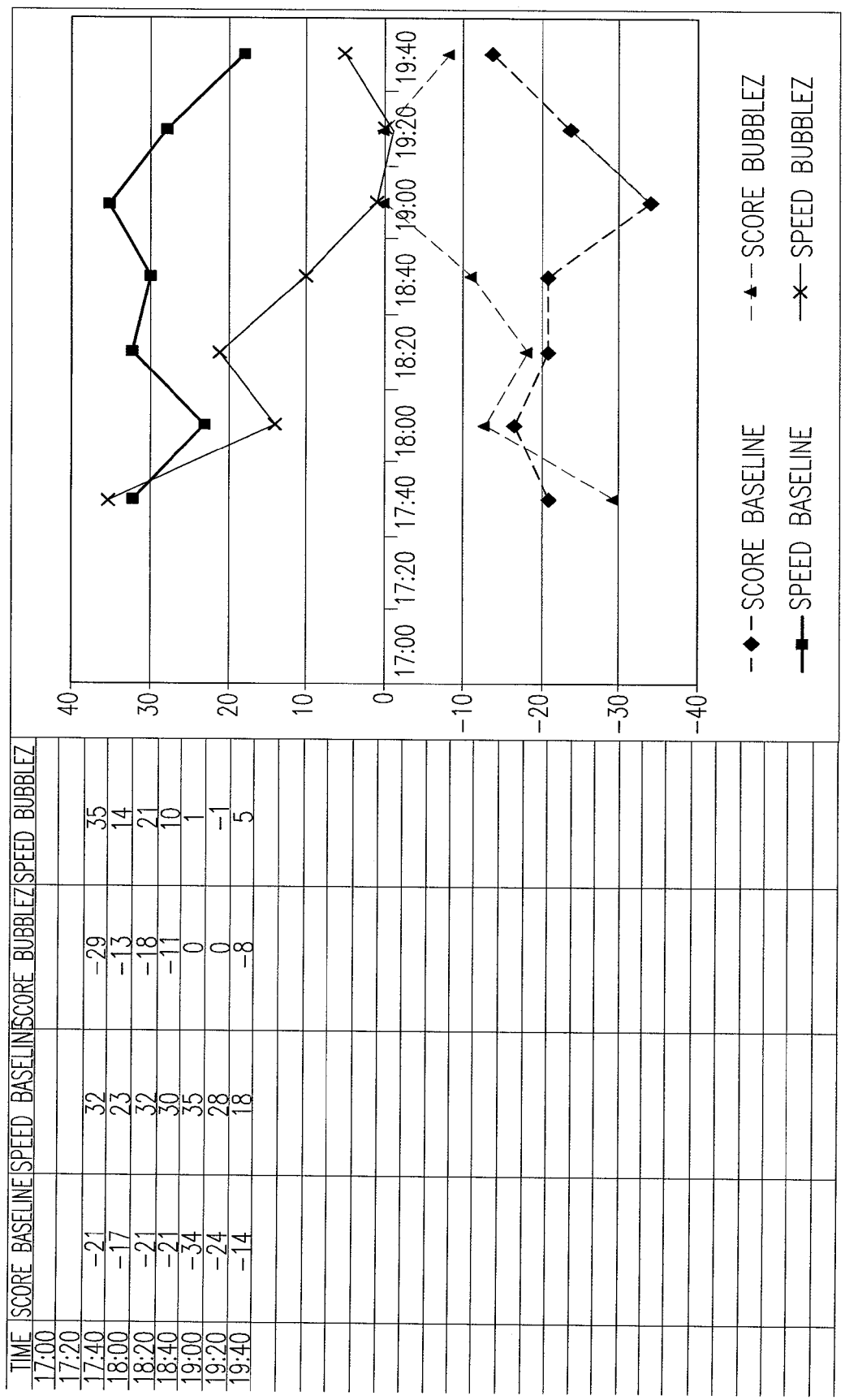
Figure 5:
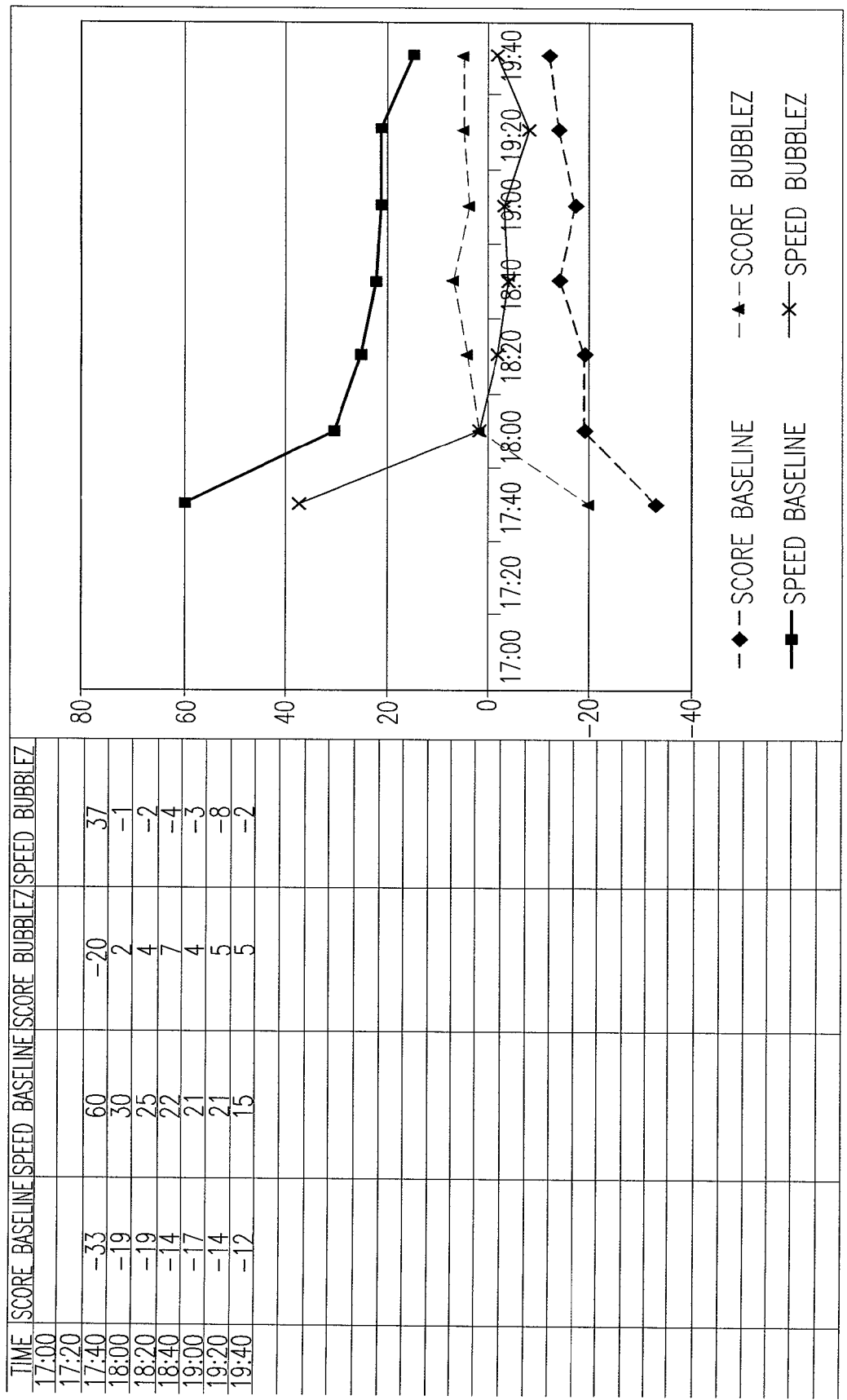
Figure 6:
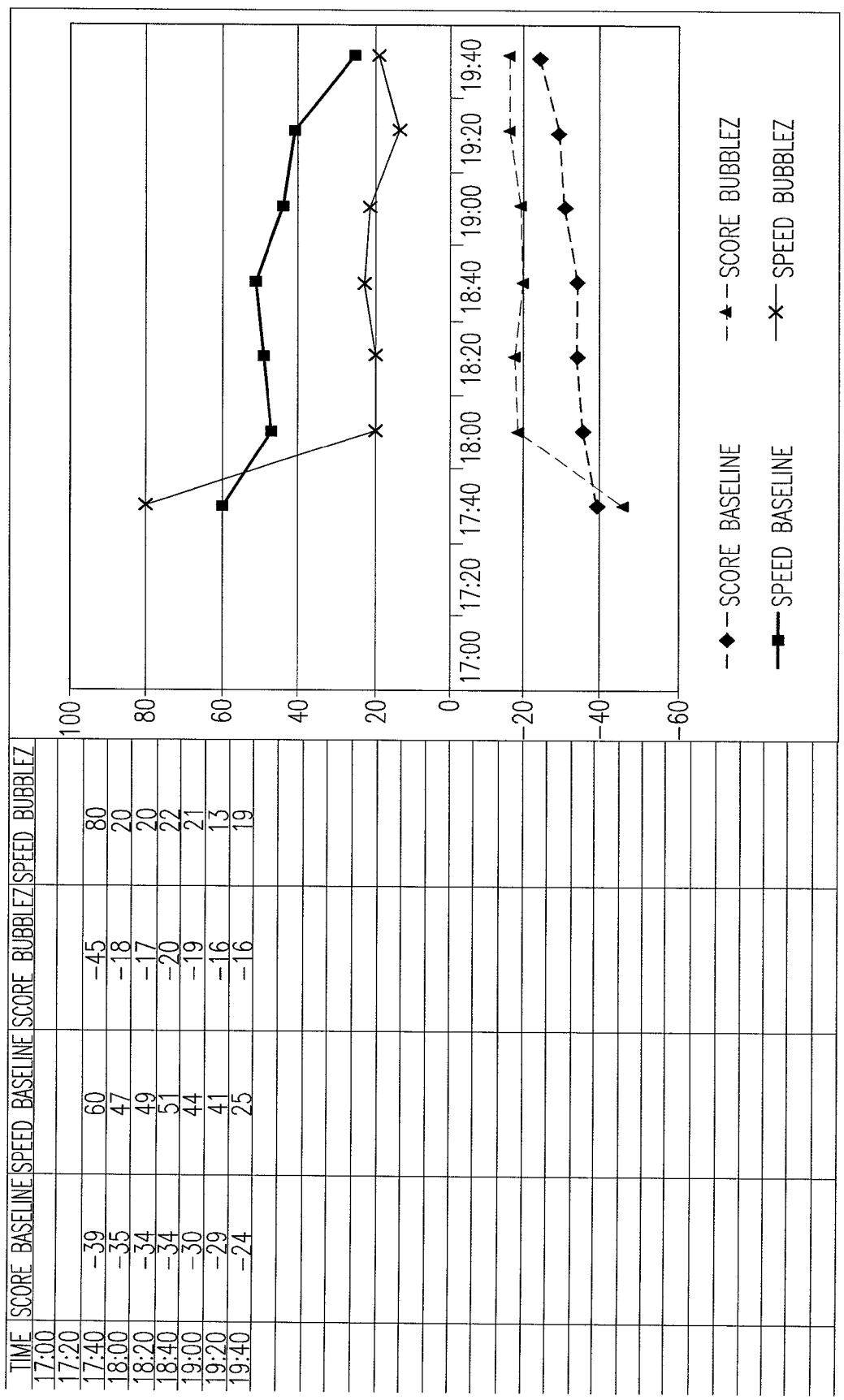

The cognitive and motor functions of the individual were evaluated using a 'lost in migration' test (FIG. 3), 'decision making' test (FIG. 4), 'spatial' test (FIG. 5) and 'speed' test (FIG. 6) using standard techniques. As is shown by the table data and graphs of these Figures, the present composition significantly reduced the time it took the individual to return to normal function, when compared to a control without the composition. In addition, the decline in performance after consuming the composition was lower when compared to the control.

Example 4

Improving Motor, Cognitive and Impulse Control in a Group of Participants Under the Influence of High Blood Alcohol A study on 24 participants (12 males and 12 females, ages 21-29), evaluated motor, cognitive and impulse control between placebo (dietary supplements with no effect on motor, cognitive and impulse control performance) and the present composition of matter. The placebo and composition sessions were scheduled at least 7 days apart to avoid interference between the sessions.

For the purpose of the study, the following motor and cognitive studies from the Lumosity web site were used:

Speed Match Overdrive (testing information processing and memory)

Color Match (testing response inhibition)

Birds in Migration (testing selective attention)

Ebb and Flow (testing task switching)

Each participant trained on each test for at least 3 hours to reach the highest level of self-proficiency and performance in order to avoid a learning curve during the study itself.

Prior to the consumption of alcohol, participants performed each test 5 times, to record the baseline performance for the specific day of testing. The 5 results were averaged to obtain a calculated score for each test.

After each participant consumed an alcohol quantity calculated to bring his/her blood alcohol level to 0.1%, every 15 minutes, a blood alcohol level was measured for each participant (using the BACtrack S75 breathalyzer) which then performed the battery of cognitive tests from the Lumosity web site. At 45 minutes following the end of alcohol consumption, each participant consumed either the placebo composition or the present composition. (Participants were told the Placebo composition was an effective composition). Each session ended 3.5 hours following the completion of alcohol consumption.

All 4 tests demonstrated advantage of the study composition arm over the placebo arm. As the 4 tests evaluated information processing+memory; inhibition, selective attention; and; task switching, it can thus be concluded that the present composition is effective in improving motor and cognitive performance in individuals under the influence of high blood alcohol (above 0.08%).

Tables 17 and 18 below present response time and normalized result (response time divided by accuracy %, generating a value representing response time in milliseconds at 100% accuracy) of placebo and present composition. The comparison time points, 15 minutes and 45 minutes, were measured from the time the participant started consuming the dietary supplements:

TABLE 17

Comparison between placebo and the present composition - reaction time (ms)

| | 15 minutes after supplements consumption | | | 45 minutes after supplements consumption | | |
|---|---|---|---|---|---|---|
| | Placebo | Composition | Diff. | Placebo | Composition | Diff. |
| Speed Match Overdrive | 664 | 645 | 19 | 650 | 630 | 20 |
| Color Match | 667 | 653 | 14 | 663 | 639 | 24 |
| Birds in Migration | 665 | 645 | 20 | 660 | 640 | 20 |
| Ebb & Flow | 580 | 568 | 12 | 575 | 562 | 13 |

The Diff. represents the advantage (or disadvantage) of the response time in the Composition study vs. the Placebo study. (All values in the table are in Milliseconds). As can be viewed from the table above, there is a consistent advantage in response time in the Composition study vs. the Placebo study.

TABLE 18

Comparison between placebo and the present composition - normalized results

| | 15 minutes after supplements consumption | | | 45 minutes after supplements consumption | | |
|---|---|---|---|---|---|---|
| | Placebo | Composition | Diff. | Placebo | Composition | Diff. |
| Speed Match Overdrive | 738 | 707 | 31 | 707 | 684 | 23 |
| Color Match | 738 | 744 | -6 | 745 | 723 | 22 |
| Birds in Migration | 724 | 705 | 19 | 731 | 705 | 26 |
| Ebb & Flow | 629 | 614 | 15 | 635 | 615 | 20 |

The Diff. value represents the advantage (or disadvantage) of the response time in the Composition study vs. the Placebo study. (All values in the table are in Milliseconds representing response time @ theoretical 100% response accuracy). As can be viewed from the table above, except in a single measurement, there is a consistent advantage in response time in the Composition study vs. the Placebo study.

Example 5

Acidic Water Resistant Micro-Encapsulation of Vitamin B2 (Core) in Zein

An experiment was conducted in order to test the release profile of encapsulated vitamin B2 in an enzyme-free, acidic environment simulating the conditions of a beverage (after reconstruction of the powdered composition).

Vitamin B2 was encapsulated with a prolamine-based coating. Prolamine proteins are water-insoluble, and edible (food-grade).

A mini (lab-scale) spray dryer Buchi B-290 equipped with an advanced inert loop under nitrogen was used to encapsulate the Vitamin B2 with a 3-fluid Buchi nozzle under the following conditions:

20 g of Vitamin B2 were dispersed in 80 g of ethanol (or water)

15 g of Zein protein was dissolved in an 80 g ethanol+20% water solution
Parameters of spraying:
Inlet temp: 1100 C
Outlet temp: 750 C
Aspirator: 100%/35 m3/h
Feed rate core/shell: 5 ml/min/10 ml/min
Spray gas flow: 50 mm
Particle size: d90~20 microns The final product was collected and placed under condition simulating the enzyme-free acidic condition of the reconstructed beverage (only acid 1.1%).

The Vitamin B2 was tested in a spectrophotometer Perkin ELMER LAMBADA 25 at wavelength 268 nanometer that is typical for Vitamin B2 absorbance.

Figure 7:
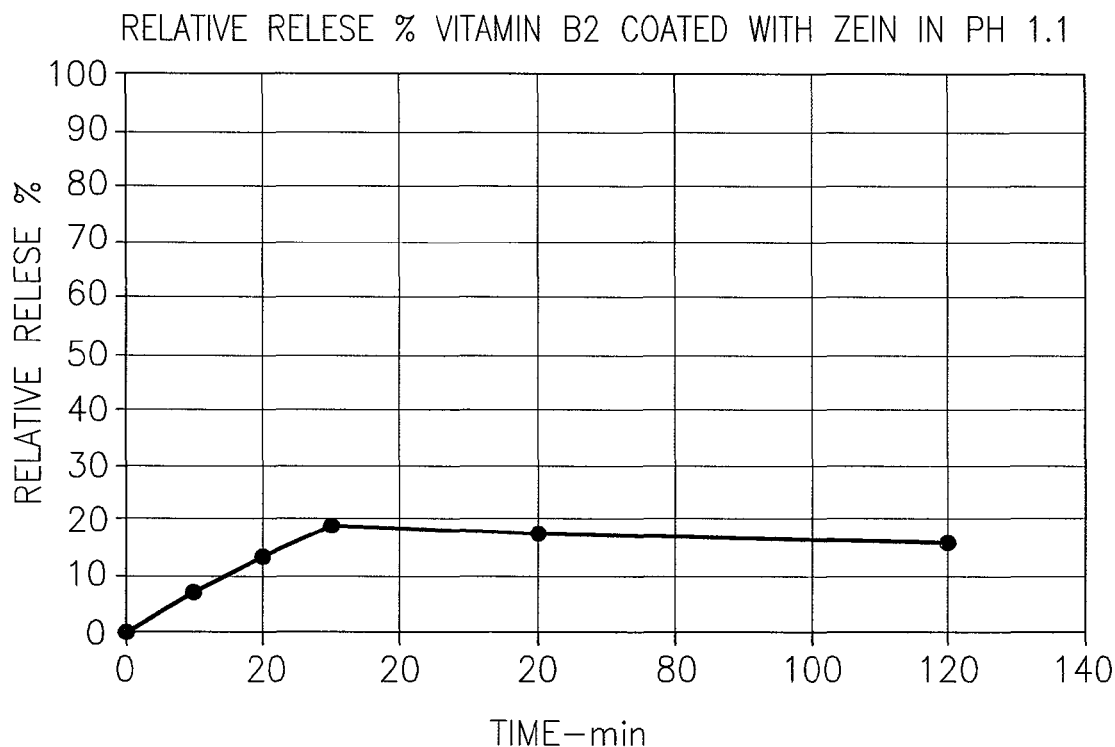
FIG. 7 is a graph showing release of Vitamin B2 in an aqueous medium having a pH of 1.1.

At the first 10 minute time mark, no release of Vitamin B2 was observed. After 20 min, ~7% was released to the surrounded media. After 30 min, ~15% was released. After 60 and 120 minutes no further release was observed (FIG. 7).

Example 6

Powders Having More Than One Microparticle Type

Composition-of-Matter 1

Figure 8A:
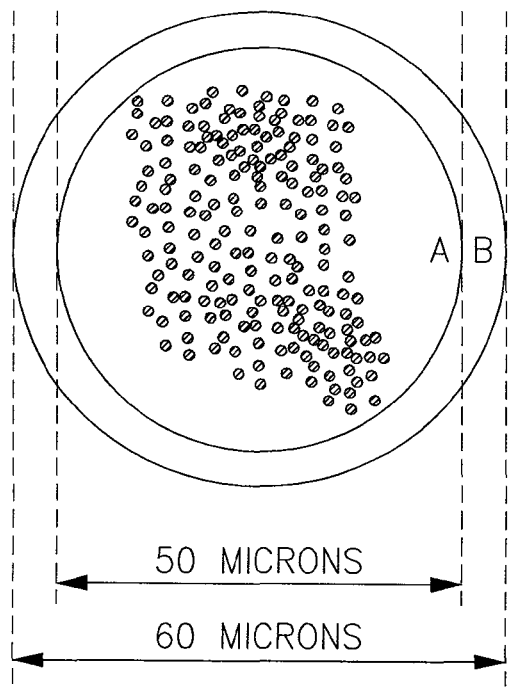
FIGS. 8A-B schematically illustrate one embodiment of a two microparticle powder of the present invention showing the active ingredient core surrounded by one or more coating layers of each particle type.
Figure 8B:
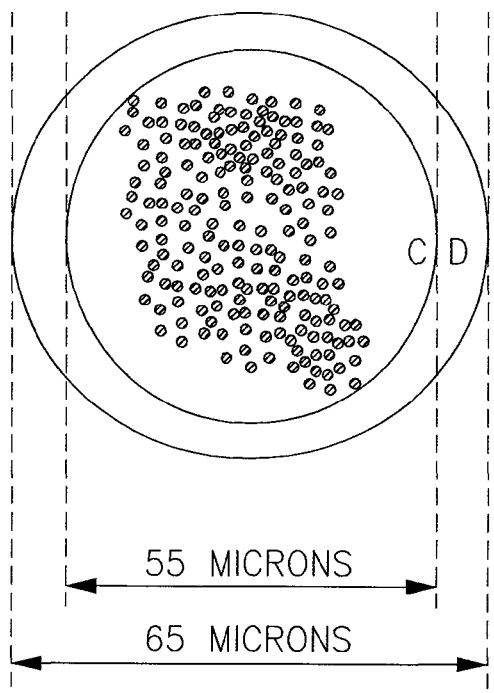

This composition-of-matter includes the two microparticle types shown in FIGS. 8a-b.

The microparticle in FIG. 8a has a core (A) with a diameter of 50 microns, and a coating layer (B) 5 microns thick, bringing the final diameter of the particle to 60 microns. The particle of FIG. 8a includes a Ginger-extract active core surrounded by a zein-based coating layer. The coating layer of this particle is designed to be materially insoluble in non-enzymatic acidic conditions of the beverage, and to rapidly dissolve in the enzymatic conditions of the stomach.

The particle of FIG. 8b has a core (C) with a diameter of 55 microns, and a coating layer (D) 5 microns thick, bringing the final diameter of the particle to 65 microns. The particle is FIG. 8b includes a Ginger extract active core surrounded by a coating layer of Shellac+HPMC. The coating layer of this particle is designed to be materially insoluble in the non-enzymatic acidic conditions of the beverage, materially insoluble in the acidic enzymatic conditions of the stomach, and to gradually dissolve in the enzymatic and pH conditions of the small intestines.

A composition-of-matter including these two microparticle types enables rapid release of the Ginger extract (from the particle in FIG. 8a) in the stomach thereby positively affecting local recovery of gastric motility through Ginger's 5-HT3 antagonistic properties, and to facilitate rapid absorption of Ginger constituents starting in the Duodenum for affecting brain receptor in the alleviation of nausea and vomiting. The later release of the Ginger extract (from the particle in FIG. 8b) in the small intestines starting from the Jejunum facilitates the continuation of Ginger constituents absorption and maintenance of its anti-emetic brain properties, Composition-of-Matter 2

Figure 9A:
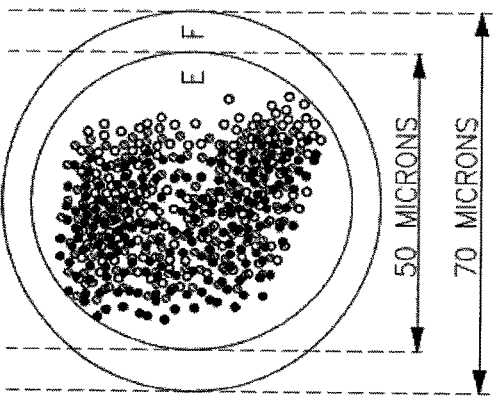
FIGS. 9A-C schematically illustrate one embodiment of a three microparticle powder of the present invention showing the active ingredient core surrounded by one or more coating layers of each particle type.
Figure 9B:
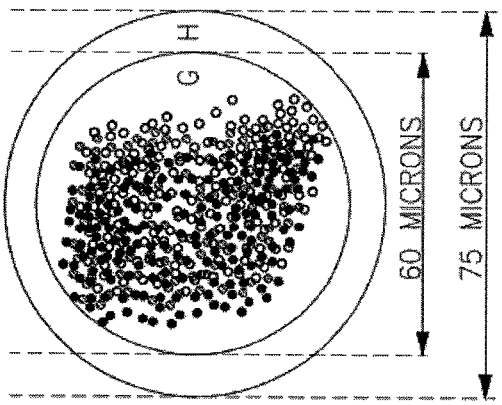
Figure 9C:
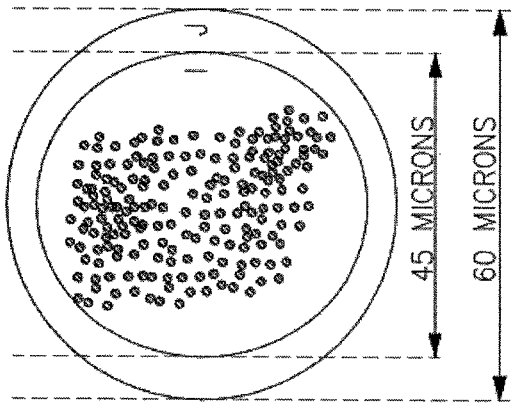

This composition-of-matter includes the three microparticle types shown in FIGS. 9a-c.

The microparticle of FIG. 9a has a core (E) with a diameter of 50 microns, and a coating layer (F) 10 microns thick, bringing the final diameter of the particle to 70 microns. The particle in FIG. 9a includes Ginger extract and Piperin in the active core surrounded by a coating layer which includes Zein and a Cellulose derivative. The coating layer of this particle is designed to be materially insoluble in non-enzymatic acidic conditions of the beverage, and to rapidly dissolve in the enzymatic conditions of the stomach.

The microparticle of FIG. 9b has a core (G) with a diameter of 60 microns, and a coating layer (H) 7.5 microns thick, bringing the final diameter of the particle to 75 microns. The particle is FIG. 9b includes Ginger extract and Piperin as the active core, surrounded by a coating layer which includes Zein and Shellac. The coating layer of this particle is designed to be materially insoluble in the non-enzymatic acidic conditions of a beverage, materially insoluble in the acidic enzymatic conditions of the stomach, and gradually dissolve in the enzymatic and pH conditions of the small intestines.

The microparticle of FIG. 9c has a core (I) with a diameter of 45 microns, and a coating layer (J) 7.5 microns thick, bringing the final diameter of the particle to 60 microns. The particle of FIG. 9c includes a Ginger extract active core surrounded by a coating layer which includes cross-linked Alginate. The coating layer of this particle is designed to be materially insoluble in the non-enzymatic acidic conditions of the beverage, materially insoluble in the acidic enzymatic conditions of the stomach, materially insoluble in the enzymatic and pH conditions of the small intestines, and, gradually dissolve in the enzymatic and pH conditions of the Colon.

A composition-of-matter including these three microparticle types enables rapid release of the Ginger extract and the Piperin (from the particle in FIG. 9a) in the stomach positively affects local recovery of gastric motility through Ginger's 5-HT3 antagonistic properties and Piperin's TRPV1 agonistic properties, and to facilitate rapid absorption of Ginger constituents starting in the Duodenum for affecting brain receptor in the alleviation of nausea and vomiting; and; to facilitate Piperin's intestinal absorption enhancement properties. The later release of the Ginger extract and Piperin (from the particle in FIG. 9b) in the small intestines starting from the Jejunum facilitates the continuation of Ginger constituents absorption and maintenance of its anti-emetic brain properties; and; Piperin's continued enhancement of intestinal absorption, The targeted Colonic release of the Ginger extract (from the particle of FIG. 9c) further facilitates its continued availability in the brain and anti-emetic action. In summary, this composition combines rapid recovery of gastric motility, enhancement of intestinal absorption and facilitation and maintenance of up to 8 hours of alleviating nausea and/or or vomiting sensations.

Composition-of-Matter 3

Figure 10A:
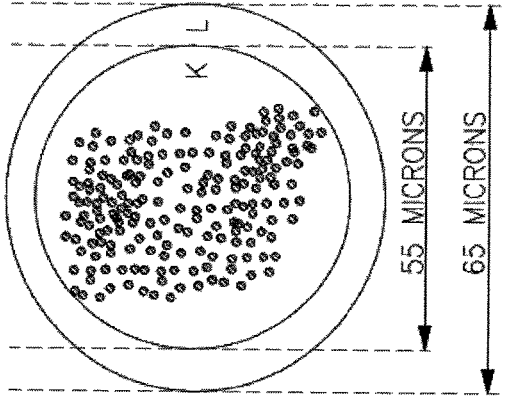
FIGS. 10A-C schematically illustrate another embodiment of a three microparticle powder of the present invention showing the active ingredient core surrounded by one or more coating layers of each particle type.
Figure 10B:
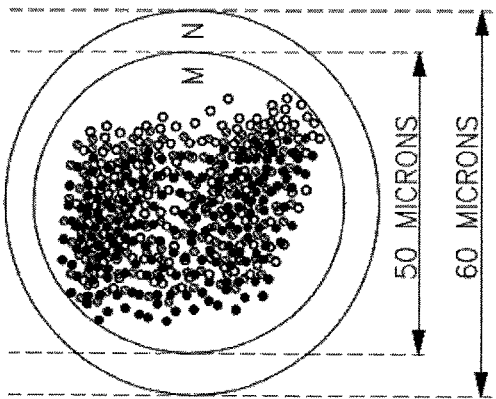
Figure 10C:
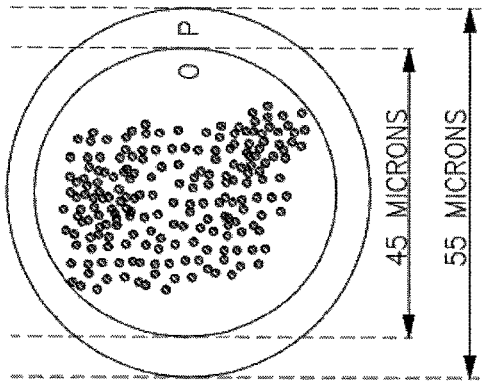

This composition-of-matter includes the three microparticle types shown in FIGS. 10a-c.

The microparticle of FIG. 10a has a core (K) with a diameter of 55 microns, and a coating layer (L) 5 microns thick, bringing the final diameter of the particle to 65 microns. The microparticle in FIG. 10a includes a Mangiferin active core surrounded by a coating layer which includes fat and Cellulose. The coating layer of this particle is designed to be materially insoluble in non-enzymatic acidic conditions of the beverage, and to rapidly dissolve in the enzymatic conditions of the stomach.

The particle of FIG. 10b has a core (M) with a diameter of 50 microns, and a coating layer (N) 5 microns thick, bringing the final diameter of the particle to 60 microns. The particle of FIG. 10b includes Mangiferin and White Willow Bark extract (Salicin) as the active core surrounded by a coating layer including Ethyl Cellulose, MCG (Medium Chain Glycerides) and Oleic Acid. The coating layer of this particle is designed to be materially insoluble in the non-enzymatic acidic conditions of the beverage, materially insoluble in the acidic enzymatic conditions of the stomach, and to gradually dissolve in the enzymatic and pH conditions of the small intestines.

The particle of FIG. 10c has a core (O) with a diameter of 45 microns, and a coating layer (P) 5 microns thick, bringing the final diameter of the particle to 55 microns. The particle of FIG. 10c includes White Willow Bark extract (Salicin) as the active core, surrounded by a coating layer including Alginate and Starch. The coating layer of this particle is designed to be materially insoluble in the non-enzymatic acidic conditions of the beverage, materially insoluble in the acidic enzymatic conditions of the stomach, materially insoluble in the enzymatic and pH conditions of the small intestines, and, gradually dissolve in the enzymatic and pH conditions of the Colon.

A composition-of-matter including these three microparticle types enables rapid release of Mangiferin (from the microparticle in FIG. 10c) in the stomach positively affecting local recovery of gastric motility of the stomach through Mangiferin's 5-HT4 agonistic properties and facilitating rapid activation of intestinal 5-HT4 receptors by Mangiferin starting in the Duodenum. The later release of the Mangiferin and Salicin (from the microparticle in FIG. 10b) in the small intestines starting from the Jejunum facilitates the continuation of Mangiferin's impact on the recovery of intestinal motility and Salicin's intestinal absorption and antagonistic action on the brain's 5-HT2 receptors, alleviating pain and headache, The targeted Colonic release of the Salicin (from the microparticle of FIG. 10c) further facilitates its continued availability in the brain and anti-headache/migraine action. In summary, this composition, with its 3 coating implementations, combines rapid recovery of gastric motility, and facilitation and maintenance of up to 8 hours of alleviating pain, headache and/or or migraine sensations.

Composition-of-Matter 4

This composition-of-matter was designed for a shelf life of over 3 months after reconstruction into an orally-deliverable gel. This composition is manufactured using a spray dryer with a 4-fluid injector, where 3 of the 4 channels are fed with fluids and/or melted fat, and single channel is utilizing air or Nitrogen, as applicable.

Figure 11C:
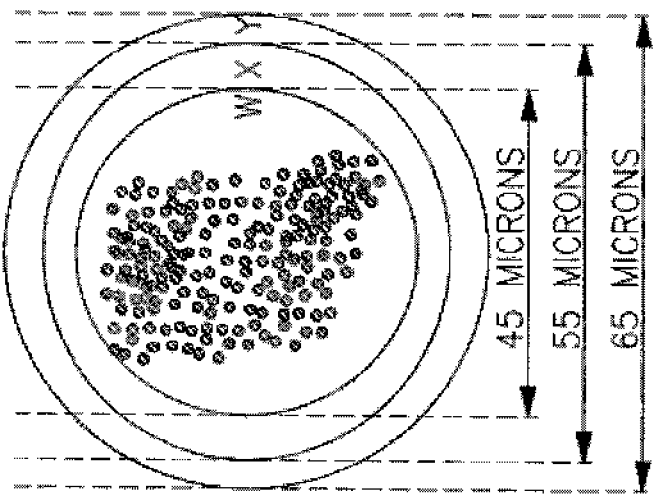
FIGS. 11A-C schematically illustrate another embodiment of a three microparticle powder of the present invention showing the active ingredient core surrounded by one or more coating layers of each particle type.
Figure 11B:
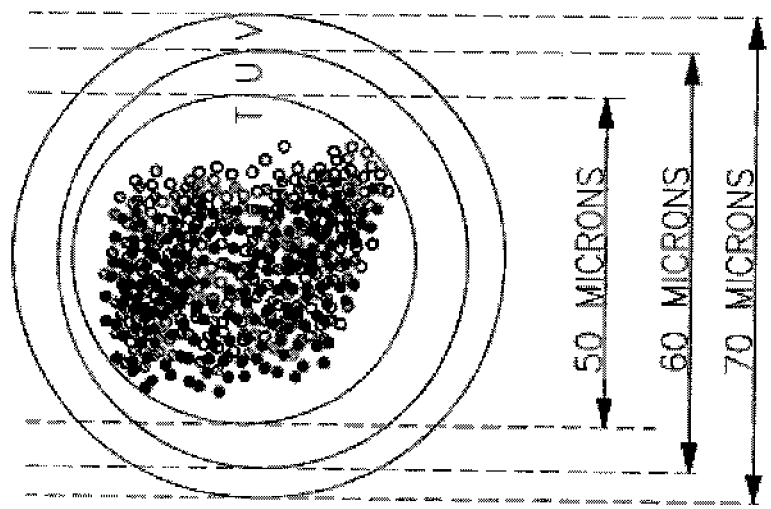
Figure 11A:
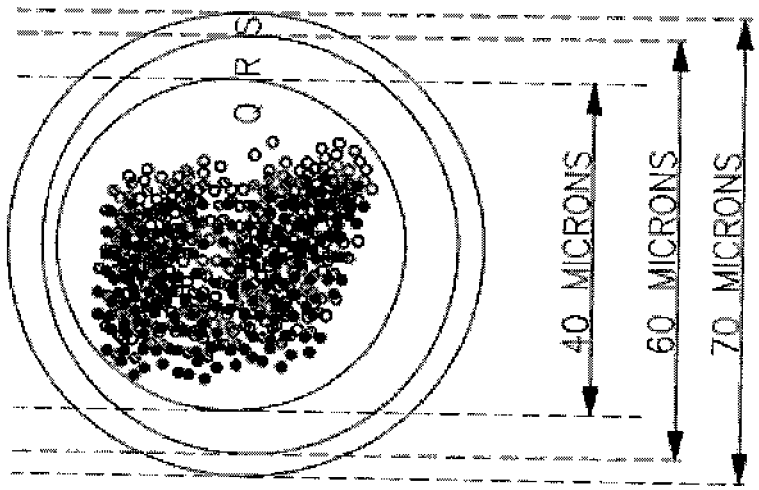

This composition-of-matter includes the three microparticle types shown in FIGS. 11a-c.

The microparticle of FIG. 11a has a core (Q) with a diameter of 40 microns, a first and inner coating layer (R) 10 microns thick, bringing the diameter of the particle to 60 microns and a second and outer coating layer (S) 5 microns thick, bringing the final diameter of the particle to 70 microns.

The microparticle of FIG. 11a includes Ginger extract and Piperin as the active core surrounded by an inner coating layer including Zein and a Cellulose derivative, and an outer coating layer including Gelatin and fat (Carnauba, Stearic acid, Sunflower). The outer coating layer improves the impermeability of the particle to acidic water and/or dissolution in acidic water-containing gel (thus providing longer shelf-life), but is quickly dissolvable in the enzymatic conditions of the stomach. The inner coating layer of this particle is designed to be materially insoluble in non-enzymatic acidic conditions of the gel, and to rapidly dissolve in the enzymatic conditions of the stomach.

The microparticle of FIG. 11b has a core (T) with a diameter of 50 microns, a first and inner coating layer (U) 10 microns thick, bringing the diameter of the particle to 60 microns and a second and outer coating layer (V) 5 microns thick, bringing the final diameter of the particle to 70 microns.

The microparticle of FIG. 11b includes Ginger extract and Piperin as the active core surrounded by an inner coating layer including Zein and Shellac, and an outer coating layer including Gelatin and fat (Carnauba, Stearic acid, Sunflower). The outer coating layer improves the impermeability of the particle to acidic water and/or dissolution in acidic water-containing gel (thus providing longer shelf-life), but is quickly dissolvable in the enzymatic conditions of the stomach. The inner coating layer of this particle is designed to be materially insoluble in the non-enzymatic acidic conditions of the gel, materially insoluble in the acidic enzymatic conditions of the stomach, and to gradually dissolve in the enzymatic and pH conditions of the small intestines.

The microparticle of FIG. 11c has a core (W) with a diameter of 45 microns, a first and inner coating layer (X) 5 microns thick, bringing the diameter of the particle to 55 microns and a second and outer coating layer (Y) 5 microns thick, bringing the final diameter of the particle to 65 microns.

The microparticle of FIG. 11c includes a Ginger extract active core surrounded by an inner coating layer of cross-linked Alginate and an outer coating layer of Gelatin and fat (Carnauba, Stearic acid, Sunflower). The outer coating layer improves the impermeability of the particle to acidic water and/or dissolution in acidic water-containing gel (thus providing longer shelf-life), but is quickly dissolvable in the enzymatic conditions of the stomach. The inner coating layer of this particle is designed to be materially insoluble in the non-enzymatic acidic conditions of the gel, materially insoluble in the acidic enzymatic conditions of the stomach, materially insoluble in the enzymatic and pH conditions of the small intestines, and gradually dissolve in the enzymatic and pH conditions of the Colon.

A composition-of-matter including these three microparticle types enables rapid release of the Ginger extract and the Piperin (from the microparticle of FIG. 11a) in the stomach positively affects local recovery of gastric motility through Ginger's 5-HT3 antagonistic properties and Piperin's TRPV1 agonistic properties, and facilitating rapid absorption of Ginger constituents starting in the Duodenum for affecting brain receptor in the alleviation of nausea and vomiting and facilitating Piperin's intestinal absorption enhancement properties. The later release of the Ginger extract and Piperin (from the microparticle in FIG. 11b) in the small intestines starting from the Jejunum facilitates the continuation of Ginger constituents absorption and maintenance of its anti-emetic brain properties and Piperin's continued enhancement of intestinal absorption. The targeted Colonic release of the Ginger extract (from the microparticle of FIG. 11c) further facilitates its continued availability in the brain and anti-emetic action. In summary, this composition, with its 3 coating implementations, combines rapid recovery of gastric motility, enhancement of intestinal absorption and facilitation and maintenance of up to 8 hours of alleviating nausea and/or or vomiting sensations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A composition-of-matter comprising at least two types of microparticles each formed from an active ingredient core encapsulated by two or more coating layers, wherein each coating layer of said coating layers is characterized by a different dissolvability profile, wherein said two or more coating layers comprise an outer coating layer and an inner coating layer, said outer coating layer and inner coating layer comprise a cellulose derivative, said outer coating layer but not said inner coating layer comprises a prolamin, said at least two types of said microparticles being differentiated by said active ingredient or said at least one coating material, wherein said composition comprises the combination of: (a) a Serotonin antagonist, (b) a COX inhibitor, (c) a Prostaglandin inhibitor, (d) an upregulator of ADH activity, and (e) an upregulator of ALDH activity, and wherein the ratio of core to said coating (w/w) is between 1:10 and 2:1.

2. The composition-of-matter of claim 1, wherein each of said at least two types of said microparticles is capable of releasing said active ingredient at a different region of a GI tract.

3. The composition-of-matter of claim 1, wherein said composition further comprises: a GABA agonist, a GABA antagonist, a Glutamate agonist, an Acetylcholine antagonist, an Adenosine antagonist, a Dopamine antagonist, a Serotonin agonist, an Anti-histamine, an up-regulator of AMPK activity, an up-regulator of SIRT activity, an up-regulator of ALDH2 activity, an up-regulator of NAD+ activity and a Vitamin B, Magnesium, Zinc, Cysteine, Alpha Lipoic Acid, Fructose, Carnitine, or any combination thereof.

4. The composition-of-matter of claim 1, wherein said composition further comprises: Bilobalide, Ginkgolides (A, B & C), Puerarin, Resveratrol, Quercetin, Curcumin, Caffeine, Theophylline, Amentoflavone, Dihydromyricetin, Copper Glycinate Chelate, Huperzine A, Rosmarinic acid, Parthenoli des, Salicin, Eriodictyol, Acetyl-Cysteine, Amentoflavone, Adiantum venestum, Amaranthus virdis, *Houttuynia cordata, Minthostachys mollis*, Sargassum fusiforme, *Usnea florida*, Limonene, Proanthocyanidins, Zinc, Sulforaphane, Menthol, Gingerols, Shogaols, Valerenic acid, Flavones, Parthenolides, or any combination thereof.

5. The composition-of-matter of claim 1, wherein said composition further comprises: Huperzine A, N-Acetyl-Cysteine, L-Carnitine, Acetyl-L-Carnitine, Glutamic acid, Glycine, L-Glutamate, L-Aspartate, L-Alanine, Magnesium salt, Zinc salt, Polygala Limonene, Tenuifolia, Acorns gramineus, *Poria cocos*, Limonene, Gingerols, Shogaols, Sulforaphane, Betaine, L-Cysteine, Mangiferin, or any combination thereof.

6. The composition-of-matter of claim 1, wherein said composition further comprises: Thunder God Vine, Resveratrol, Quercetin, Kaempferol, Pycogenol, Parthenolides, EGCG, Ursolic acid, Berberine, Ginsenosides, Gingerols, Shogaols, Salicin and Hesperidin, Vitamin C, Mangosteen, Butterbur, or any combination thereof.

7. The composition-of-matter of claim 1, wherein said composition further comprises: Shogaols, Piperin, Omega-3, Echinacea, Carvone, Camphor, Mustard oil, Carnosol, or any combination thereof.

8. The composition-of-matter of claim 1, wherein said composition further comprises: Pantethine, Vitamin D, Vitamin E, TMG (Betaine), Choline salt, SAMe, Nicotinamide, Folate/Folic acid, Co-enzyme A, Proanthocyanidines, Cysteinylglycine, Magnesium salt, Sulforaphane, L-Cysteine, N-Acetyl-Cysteine, Resveratrol, Quercetin, Caffeine, Theophylline, L-Carnitine, Acetyl-L-Carnitine, Pyruvate salt, Fructose, Bilobalide, Puerarin, Shogaols, Salicin, Sulforaphane, Menthol, Curcumin, Sulforaphane, or any combination thereof.

9. The composition-of-matter of claim 1, wherein said cellulose derivative is at least one selected from the group consisting of hydroxypropyl methylcellulose (HPMC), Ethyl Cellulose and Methyl Cellulose.

10. The composition-of-matter of claim 1, further comprising a non-encapsulated active ingredient.

11. The composition-of-matter of claim 1, wherein the prolamin is selected from the group consisting of zein and wheat prolamin.

12. A beverage, shake or gel comprising a dispersion of the composition-of-matter of claim 1 in an aqueous medium.

13. The beverage of claim 12, wherein a pH of said beverage is 2.4-3.5.

14. An article of manufacturing comprising a container having two environmentally isolated compartments, a first compartment including the composition-of-matter of claim 1 and a second compartment including a liquid.

15. The article of manufacturing of claim 14, wherein said container is constructed so as to enable mixing of said composition-of-matter with said liquid to generate a consumable suspension.

16. The article of manufacturing of claim 14, wherein the composition further comprises: Bilobalide, Ginkgolides, Amentoflavone, Dihydromyricetin, Puerarin, Limonene, Huperzine, Quercetin, White Willow Bark, Feverfew, Grape Seed Extract, Alpha Lipoic Acid, Co-Enzyme A, or any combination thereof.

* * * * *